(12) United States Patent
Mizokuchi et al.

(10) Patent No.: US 12,066,435 B2
(45) Date of Patent: Aug. 20, 2024

(54) MICRODEVICE AND ANALYSIS DEVICE

(71) Applicant: Tianma Japan, Ltd., Kanagawa (JP)

(72) Inventors: Chikaaki Mizokuchi, Kanagawa (JP); Koji Shigemura, Kanagawa (JP); Ken Sumiyoshi, Kanagawa (JP)

(73) Assignee: TIANMA JAPAN, LTD., Kanagawa (JP)

( * ) Notice: Subject to any disclaimer, the term of this patent is extended or adjusted under 35 U.S.C. 154(b) by 0 days.

(21) Appl. No.: 17/383,557

(22) Filed: Jul. 23, 2021

(65) Prior Publication Data

US 2022/0034876 A1 Feb. 3, 2022

(30) Foreign Application Priority Data

Jul. 29, 2020 (JP) .................. 2020-128025

(51) Int. Cl.
*G01N 33/543* (2006.01)
*G01N 21/64* (2006.01)
*G02B 21/16* (2006.01)

(52) U.S. Cl.
CPC ... *G01N 33/54373* (2013.01); *G01N 21/6428* (2013.01); *G01N 21/6456* (2013.01);
(Continued)

(58) Field of Classification Search
CPC .................................................. B01L 3/5027
See application file for complete search history.

(56) References Cited

U.S. PATENT DOCUMENTS

2010/0233030 A1* 9/2010 Murphy ........... G01N 33/54366 422/69
2010/0261205 A1 10/2010 Kakuta et al.
(Continued)

FOREIGN PATENT DOCUMENTS

CN 109456879 A * 3/2019 ............ C12M 23/16
JP 03-103765 A 4/1991
(Continued)

OTHER PUBLICATIONS

Fu, Xiaotong, Nicholas Mavrogiannis, Markela Ibo, Francesca Crivellari, and Zachary R. Gagnon. "Microfluidic free-flow zone electrophoresis and isotachophoresis using carbon black nano-composite PDMS sidewall membranes." Electrophoresis 38, No. 2 (2017): 327-334. (Year: 2017).*

(Continued)

*Primary Examiner* — Matthew D Krcha
*Assistant Examiner* — Ryan J Dowty
(74) *Attorney, Agent, or Firm* — Sughrue Mion, PLLC

(57) ABSTRACT

A microdevice includes: a microchannel to which a measurement target solution containing a measurement target substance is introduced; an antibody being fixed to at least one sidewall surface of the microchannel and specifically binding to the measurement target substance; a fluorescence-labeled derivative being specifically bound to the antibody and being acquired by fluorescence-labeling the measurement target substance; and a light blocker blocking excitation light exciting fluorescent light radiated by the fluorescence-labeled derivative. The measurement target substance and the fluorescence-labeled derivative specifically bind to the antibody in a competitive manner, and the antibody is fixed to the sidewall surface of the microchannel in a state of specifically binding to the fluorescence-labeled derivative. The light blocker blocks the excitation light entering the fluorescence-labeled derivative specifically binding to the antibody.

18 Claims, 15 Drawing Sheets

(52) U.S. Cl.
CPC ..... *G02B 21/16* (2013.01); *G01N 2021/6439* (2013.01); *G01N 2201/062* (2013.01)

(56) References Cited

U.S. PATENT DOCUMENTS

2011/0114190 A1* 5/2011 Wen ................. B01L 3/0265
422/504
2018/0203008 A1 7/2018 Takahashi

FOREIGN PATENT DOCUMENTS

| JP | 2006-170853 A | 6/2006 |
| JP | 4717081 B2 | 7/2011 |
| WO | 2017/056748 A1 | 4/2017 |

OTHER PUBLICATIONS

Hiremath, Shivashankar, Micro & Nano Letters, 2020, vol. 15, Iss. 7, pp. 437-440, "Photomechanical actuation of polydimethylsiloxane/ carbon black nanocomposite".
Li, Hui, Scientific Reports 2020, 10, 4639, "A Supersensitive, Multidimensional Flexible Strain Gauge Sensor Based on Ag/PDMS for Human Activities Monitoring".

\* cited by examiner

MICRODEVICE AND ANALYSIS DEVICE

CROSS-REFERENCE TO RELATED APPLICATION

This application claims the benefit of Japanese Patent Application No. 2020-128025, filed on Jul. 29, 2020, the entire disclosure of which is incorporated by reference herein.

FIELD

This application relates generally to a microdevice and an analysis device.

BACKGROUND

A fluorescence polarization immunoassay (FPIA) detecting a measurement target substance by using an antigen-antibody reaction is known as an immunoassay using fluorescent light. For example, Unexamined Japanese Patent Application Publication No. H3-103765 discloses a method of determining the concentration of a measured antigen (measurement target substance) from the degree of polarization of measured fluorescent light.

Further, a method of producing an antigen-antibody reaction in a microchannel in a microdevice is known. The reaction time of an antigen-antibody reaction can be shortened by producing the antigen-antibody reaction in a microchannel. For example, Japanese Patent No. 4717081 discloses an immunoassay microchip in which a microstructure is placed in a channel. The microstructure holds a bead, a primary antibody being solid phased on the surface of the bead.

For example, in a fluorescence polarization immunoassay using a conventional microdevice, a solution containing a measurement target substance and a fluorescence-labeled derivative acquired by labeling the measurement target substance with a fluorescent substance is introduced to a channel to which an antibody is fixed. After a competitive reaction (antigen-antibody reaction) to the antibody between the measurement target substance and the fluorescence-labeled derivative reaches an equilibrium state, the solution in the channel is irradiated by linearly polarized excitation light exciting fluorescent light radiated by the fluorescence-labeled derivative, and the degree of polarization of fluorescent light radiated from the solution is determined. The degree of polarization of fluorescent light varies with the concentration of the measurement target substance, and therefore the concentration of the measurement target substance can be acquired from a previously generated calibration curve.

In the fluorescence polarization immunoassay using a conventional microdevice, fluorescent light radiated from the solution includes fluorescent light radiated by a fluorescence-labeled derivative specifically binding to the antibody and fluorescent light radiated by a fluorescence-labeled derivative not binding to the antibody, and therefore measurement sensitivity is low.

SUMMARY

A microdevice according to a first aspect of the present disclosure includes:
a microchannel to which a measurement target solution containing a measurement target substance is introduced;
an antibody being fixed to at least one sidewall surface of the microchannel and specifically binding to the measurement target substance;
a fluorescence-labeled derivative being specifically bound to the antibody and being acquired by fluorescence-labeling the measurement target substance; and
a light blocker blocking excitation light exciting fluorescent light radiated by the fluorescence-labeled derivative, wherein
the measurement target substance and the fluorescence-labeled derivative specifically bind to the antibody in a competitive manner,
the antibody is fixed to the sidewall surface of the microchannel in a state of specifically binding to the fluorescence-labeled derivative, and
the light blocker blocks the excitation light entering the fluorescence-labeled derivative specifically binding to the antibody.

A microdevice according to a second aspect of the present disclosure includes:
a microchannel to which a measurement target solution containing a measurement target substance and a fluorescence-labeled derivative acquired by fluorescence-labeling the measurement target substance is introduced;
an antibody being fixed to at least one sidewall surface of the microchannel and specifically binding to the measurement target substance and the fluorescence-labeled derivative; and
a light blocker blocking excitation light exciting fluorescent light radiated by the fluorescence-labeled derivative, wherein
the measurement target substance and the fluorescence-labeled derivative specifically bind to the antibody in a competitive manner, and,
when the measurement target solution is introduced to the microchannel, the light blocker blocks the excitation light entering the fluorescence-labeled derivative specifically binding to the antibody.

An analysis device according to a third aspect of the present disclosure includes:
one of the aforementioned microdevices;
an irradiator irradiating the microdevice with the excitation light; and
a detector detecting the fluorescent light.

It is to be understood that both the foregoing general description and the following detailed description are exemplary and explanatory and are not restrictive of this disclosure.

BRIEF DESCRIPTION OF THE DRAWINGS

A more complete understanding of this application can be obtained when the following detailed description is considered in conjunction with the following drawings, in which.

DETAILED DESCRIPTION

Microdevices according to embodiments will be described below with reference to drawings.

Embodiment 1

A microdevice 10 according to the present embodiment will be described with reference to FIG. 1 to FIG. 8. For example, the microdevice 10 is used for detecting a measurement target substance Ag1 by using a fluorescence polarization immunoassay.

Figure 1:
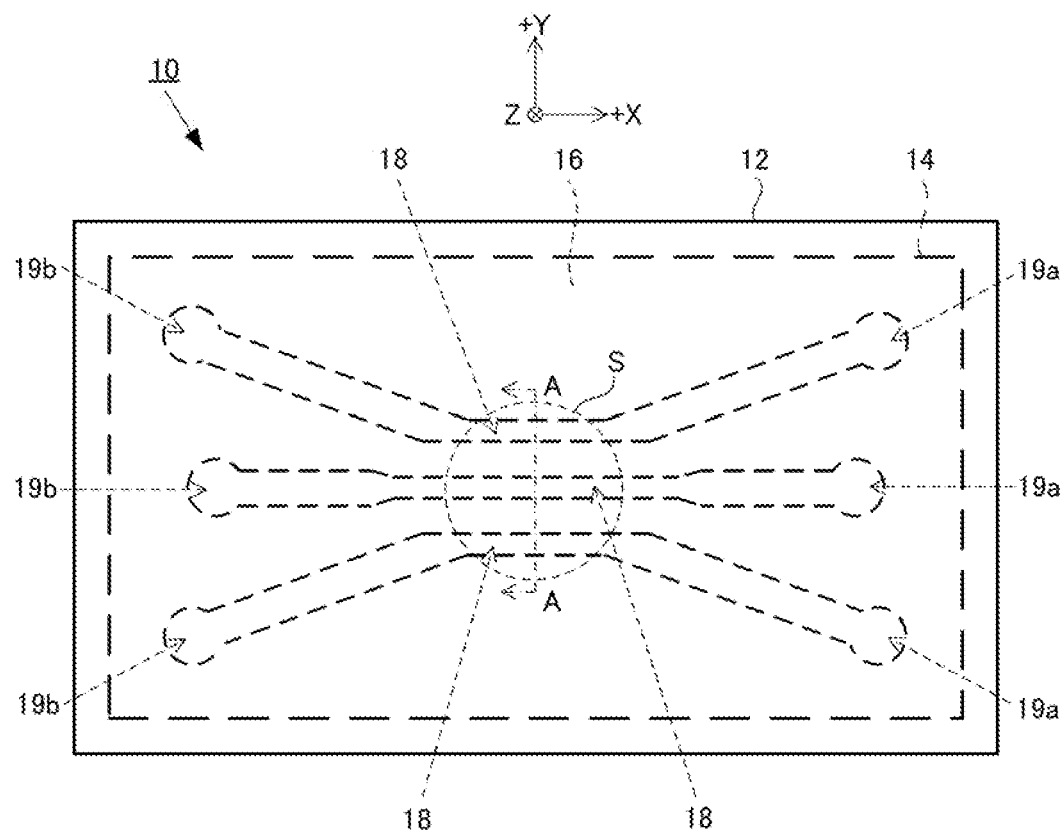
FIG. 1 is a top view illustrating a microdevice according to Embodiment 1.
Figure 2:
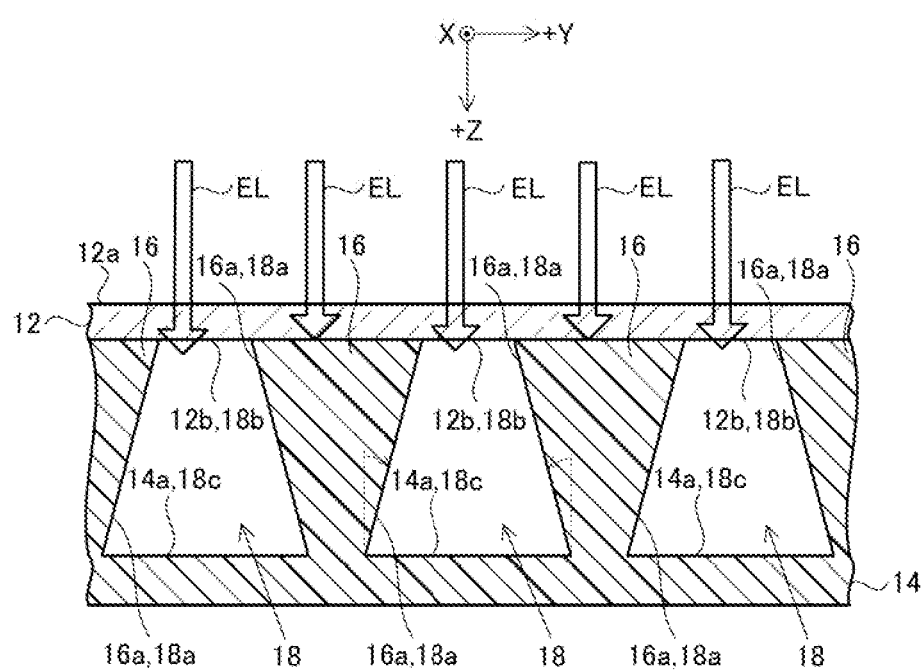
FIG. 2 is a cross-sectional view of the microdevice illustrated in FIG. 1 taken along a line A-A.
Figure 3:
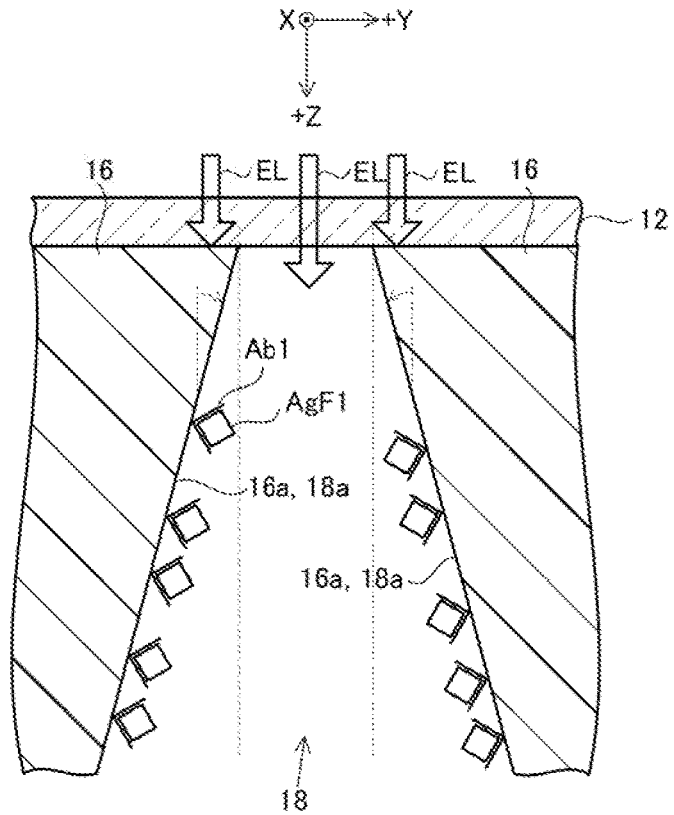
FIG. 3 is a schematic diagram illustrating an antibody and a fluorescence-labeled derivative according to Embodiment 1.

As illustrated in FIG. 1 and FIG. 2, the microdevice 10 includes a first substrate 12, a second substrate 14, a first light blocker 16, and three microchannels 18. Furthermore, as illustrated in FIG. 3, the microdevice 10 includes an antibody Ab1 and a fluorescence-labeled derivative AgF1. The fluorescence-labeled derivative AgF1 is a derivative acquired by fluorescence-labeling the measurement target substance Ag1 with a fluorescent substance.

The first substrate 12 and the second substrate 14 sandwich the first light blocker 16. The first light blocker 16 blocks excitation light EL exciting fluorescent light FL radiated by the fluorescence-labeled derivative AgF1. Further, the first substrate 12, the second substrate 14, and the first light blocker 16 form the microchannel 18. A measurement target solution containing the measurement target substance Ag1 is introduced to the microchannel 18. The antibody Ab1 is fixed to a sidewall surface 18a of the microchannel 18. The fluorescence-labeled derivative AgF1 specifically binds to the antibody Ab1.

For ease of understanding, the rightward direction (toward the right-hand side of the page) of the microdevice 10 in FIG. 1 is herein denoted as a +X-direction, the upward direction (toward the top of the page) is denoted as a +Y-direction, and a direction perpendicular to the +X-direction and the +Y-direction (toward the back of the page) is denoted as a +Z-direction. Further, the antibody Ab1 and the fluorescence-labeled derivative AgF1 are omitted in FIG. 1 and FIG. 2.

The first substrate 12 in the microdevice 10 is a plate-like silica glass substrate. As illustrated in FIG. 2, excitation light EL enters the microdevice 10 from the first substrate 12.

The excitation light EL is light exciting fluorescent light FL radiated by the fluorescence-labeled derivative AgF1. In the present embodiment, the excitation light EL irradiates an irradiation region S illustrated in FIG. 1. The excitation light EL enters perpendicularly to a first principal plane 12a of the first substrate 12.

The second substrate 14 in the microdevice 10 is a plate-like substrate. The second substrate 14 is formed of a material with low autofluorescence. In the present embodiment, the second substrate 14 is formed of polydimethylsiloxane (PDMS) containing carbon black. The second substrate 14 faces the first substrate 12. The second substrate 14 and the first substrate 12 sandwich the first light blocker 16.

The first light blocker 16 in the microdevice 10 forms the microchannel 18 by being sandwiched between the first substrate 12 and the second substrate 14 and blocks excitation light EL entering from the first substrate 12. The first light blocker 16 absorbs excitation light EL exciting fluorescent light FL radiated by the fluorescence-labeled derivative AgF1 and is formed of a material with low autofluorescence. In the present embodiment, the first light blocker 16 is integrally formed of polydimethylsiloxane containing carbon black with the second substrate 14.

When viewed at a section of the microchannel 18 in a widthwise direction (YZ plane), a side 16a of the first light blocker 16 forms a sidewall surface 18a of the microchannel 18. In the present embodiment, the two sides 16a forming the two sidewall surfaces 18a of the microchannel 18 incline in a direction narrowing the width (that is, the length in the Y-direction) of the microchannel 18 toward the first substrate 12. In other words, the two sides 16a incline in a direction getting close to each other toward the first substrate 12. As illustrated in FIG. 3, the antibody Ab1 is fixed to the side 16a of the first light blocker 16 (that is, the sidewall surface 18a of the microchannel 18) in a state of specifically binding to the fluorescence-labeled derivative AgF1.

In the present embodiment, the side 16a of the first light blocker 16 inclines in a direction narrowing the width of the microchannel 18 toward the first substrate 12, and excitation light EL enters from the first substrate 12 perpendicularly to the first principal plane 12a. Accordingly, as illustrated in FIG. 3, the first light blocker 16 blocks excitation light EL entering the fluorescence-labeled derivative AgF1 specifically binding to the antibody Ab1 fixed to the side 16a, that is, the sidewall surface 18a of the microchannel 18. For ease of understanding, the fluorescence-labeled derivative specifically binding to the antibody fixed to the sidewall surface 18a may be hereinafter described as a bound fluorescence-labeled derivative.

The microchannels 18 in the microdevice 10 extend in parallel with one another in the X-direction in the irradiation region S. A measurement target solution containing the measurement target substance Ag1 is introduced to the microchannel 18. The measurement target substance Ag1 has only to be a compound that can be detected by an immunoassay using fluorescent light. Examples of the measurement target substance Ag1 include an antibiotic, a physiologically active substance, and mycotoxin. Specific examples of the measurement target substance Ag1 include prostaglandin E2, β-lactoglobulin, chloramphenicol, and deoxynivalenol. The measurement target solution containing the measurement target substance Ag1 is introduced to the microchannel 18 from an inlet 19a. The inlet 19a passes through the second substrate 14 and the first light blocker 16 and connects to the microchannel 18. Further, the measurement target solution within the microchannel 18 is discharged from an outlet 19b. The outlet 19b passes through the second substrate 14 and the first light blocker 16 and connects to the microchannel 18. For ease of understanding, a measurement target solution containing a measurement target substance may be hereinafter described as a measurement target solution.

The microchannel 18 is formed by the first substrate 12, the second substrate 14, and the first light blocker 16. An upper wall surface 18b of the microchannel 18 is formed by a second principal plane 12b of the first substrate 12. A lower wall surface 18c of the microchannel 18 is formed by a first principal plane 14a of the second substrate 14. The sidewall surface 18a of the microchannel 18 is formed by the side 16a of the first light blocker 16. The sides 16a of the first light blocker 16 incline in a direction narrowing the width of the microchannel 18 toward the first substrate 12, and therefore the two sidewall surfaces 18a of the microchannel 18 also incline in a direction narrowing the width of the microchannel 18 toward the first substrate 12. In other words, the two sidewall surfaces 18a incline in a direction getting close to each other toward the first substrate 12. As illustrated in FIG. 3, the antibody Ab1 is fixed to the sidewall surface 18a of the microchannel 18 (that is, the side 16a of the first light blocker 16).

In the present embodiment, the sidewall surfaces 18a incline in a direction narrowing the width of the microchannel 18 toward the first substrate 12, and therefore a section of the microchannel 18 in a widthwise direction (Y-direction) has a tapered shape narrowing toward the first substrate 12. For example, the width of the microchannel 18 is 210 μm in the widest part and 50 μm in the narrowest part. For example, the depth (the length in the Z-direction) of the microchannel 18 is 900 μm. Further, the ratio of the depth of the microchannel 18 to the narrowest width of the microchannel 18 is preferably 2 or greater.

The antibody Ab1 in the microdevice 10 is fixed to the sidewall surface 18a of the microchannel 18 (that is, the side 16a of the first light blocker 16). In the present embodiment, the antibody Ab1 is fixed to the sidewall surface 18a of the microchannel 18 in a state of specifically binding to the fluorescence-labeled derivative AgF1. The antibody Ab1 specifically binds to the measurement target substance Ag1 by an antigen-antibody reaction. For example, the antibody Ab1 is acquired by inoculating the measurement target substance Ag1 into a host animal (such as a mouse or a cow) and then collecting and refining an antibody in blood produced by the host animal. Further, a commercially available antibody can also be used as the antibody Ab1.

The fluorescence-labeled derivative AgF1 in the microdevice 10 is specifically bound to the antibody Ab1 by an antigen-antibody reaction. The fluorescence-labeled derivative AgF1 is acquired by binding a fluorescent substance to the measurement target substance Ag1 by using a generally known method. Examples of the fluorescent substance include fluorescein (wavelength of excitation light EL: 494 nm, wavelength of fluorescent light FL: 521 nm) and rhodamine β (wavelength of excitation light EL: 550 nm, wavelength of fluorescent light FL: 580 nm). In the present embodiment, the first light blocker 16 blocks excitation light EL, and therefore even when the microdevice 10 is irradiated by excitation light EL, the fluorescence-labeled derivative AgF1 specifically binding to the antibody Ab1 fixed to the sidewall surface 18a (bound fluorescence-labeled derivative AgF1) does not radiate fluorescent light.

An operation of the microdevice 10 will be described.

Figure 4:
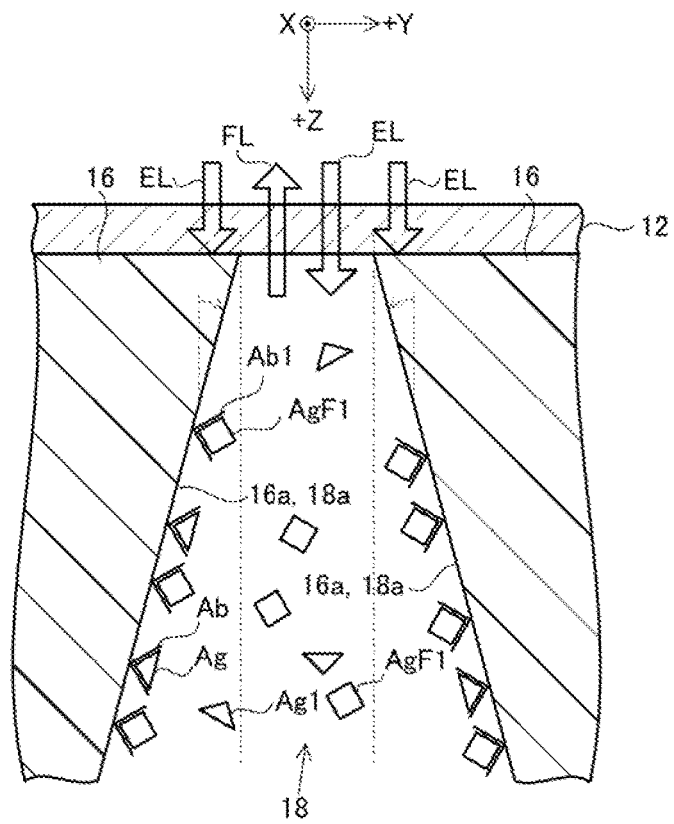
FIG. 4 is a schematic diagram for illustrating an operation of the microdevice according to Embodiment 1.

When a measurement target solution is introduced to the microchannel 18 in the microdevice 10, the measurement target substance Ag1 contained in the measurement target solution specifically binds to the antibody Ab1 by an antigen-antibody reaction in competition with the fluorescence-labeled derivative AgF1. Then, as illustrated in FIG. 4, a fluorescence-labeled derivative AgF1 not specifically binding to the antibody Ab1 is produced in the microchannel 18. When a competitive reaction to the antibody Ab1 between the measurement target substance Ag1 and the fluorescence-labeled derivative AgF1 reaches an equilibrium state, the fluorescence-labeled derivative AgF1 not specifically binding to the antibody Ab1 is produced in the microchannel 18 in an amount according to the concentration of the measurement target substance Ag1. For ease of understanding, a fluorescence-labeled derivative not specifically binding to an antibody may be hereinafter described as a free fluorescence-labeled derivative.

When excitation light EL enters from the first substrate 12 after the competitive reaction reaches an equilibrium state, the first light blocker 16 blocks the excitation light EL entering a bound fluorescence-labeled derivative AgF1, and therefore fluorescent light radiated by the bound fluorescence-labeled derivative AgF1 is suppressed, and fluorescent light radiated by a free fluorescence-labeled derivative AgF1 is measured. Accordingly, the microdevice 10 can improve measurement sensitivity to the measurement target substance Ag1.

Figure 5:
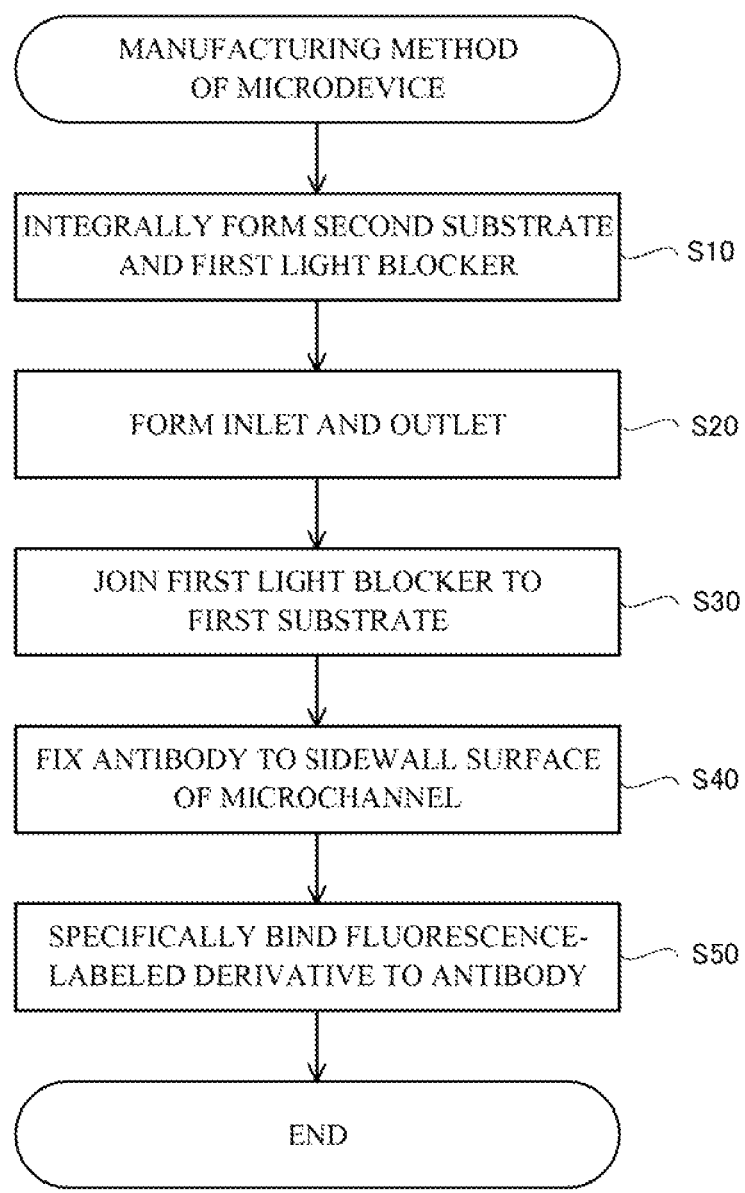
FIG. 5 is a flowchart illustrating a manufacturing method of the microdevice according to Embodiment 1.

Next, a manufacturing method of the microdevice 10 will be described with reference to FIG. 5 and FIG. 6. FIG. 5 is a flowchart illustrating the manufacturing method of the microdevice 10. The manufacturing method of the microdevice 10 includes a process of integrally forming the second substrate 14 and the first light blocker 16 (Step S10), a process of forming the inlet 19a and the outlet 19b (Step S20), a process of joining the first light blocker 16 to the first substrate 12 (Step S30), a process of fixing the antibody Ab1 to the sidewall surface 18a of the microchannel 18 (Step S40), and a process of specifically binding the fluorescence-labeled derivative AgF1 to the antibody Ab1 (Step S50).

Figure 6:
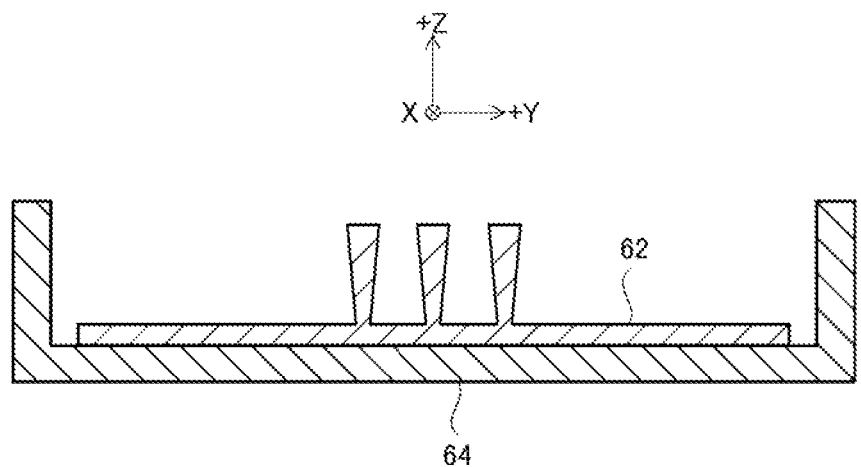
FIG. 6 is a schematic diagram for illustrating a process of integrally forming a second substrate and a light blocker according to Embodiment 1.

In Step S10, a mold 62 suited to the shape of the second substrate 14 and the first light blocker 16 is placed in a form 64, as illustrated in FIG. 6. Then, polydimethylsiloxane resin containing carbon black is poured into the form 64. By curing the polydimethylsiloxane resin poured into the form 64, the second substrate 14 and the first light blocker 16 are integrally formed. For example, the mold 62 is produced by photolithographically treating a silicon substrate. Further, a member being an integral formation of the second substrate 14 and the first light blocker 16 may be hereinafter described as the second substrate 14 including the first light blocker 16.

Returning to FIG. 5, in Step S20, the inlet 19a and the outlet 19b are formed by making through holes at predetermined positions on the second substrate 14 including the first light blocker 16 by using a jig.

In Step S30, the first light blocker 16 is joined to the first substrate 12 by placing the first substrate 12 on the first light blocker 16 and then pressing the first substrate 12 against the first light blocker 16. Consequently, the first substrate 12, the second substrate 14, and the first light blocker 16 form the microchannel 18.

In Step S40, a solution containing the antibody Ab1 is introduced to the microchannel 18, and the antibody Ab1 is fixed to the sidewall surface 18a of the microchannel 18 (the side 16a of the first light blocker 16). After the antibody Ab1 is fixed to the sidewall surface 18a of the microchannel 18, a predetermined solution is introduced to the microchannel 18, and the inside of the microchannel 18 is washed. A physical adsorption method, a generally known method of covalently bonding or ionically bonding the antibody Ab1 to the sidewall surface 18a, or the like may be used according to a characteristic of the antibody Ab1 as the method of fixing the antibody Ab1.

In Step S50, a solution containing the fluorescence-labeled derivative AgF1 is introduced to the microchannel 18, and the fluorescence-labeled derivative AgF1 is specifically bound to the antibody Ab1 by an antigen-antibody reaction. After the fluorescence-labeled derivative AgF1 is bound to the antibody Ab1, a predetermined solution is introduced to the microchannel 18, and the inside of the microchannel 18 is washed. Thus, the microdevice 10 can be produced.

Detection of the measurement target substance Ag1 using the microdevice 10 will be described. First, an analysis device 100 detecting the measurement target substance Ag1 will be described.

Figure 7:
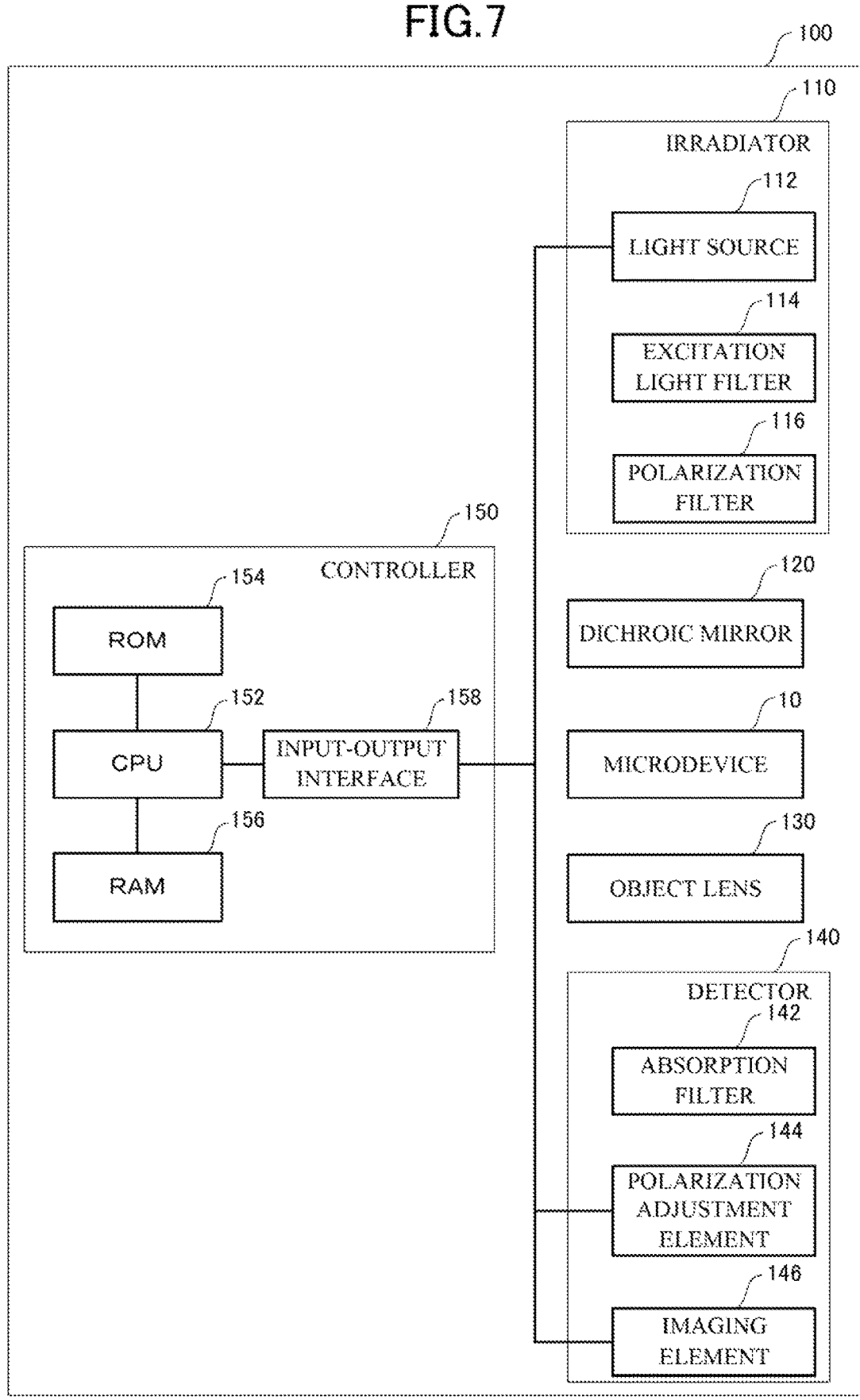
FIG. 7 is a diagram illustrating a configuration of an analysis device according to Embodiment 1.
Figure 8:
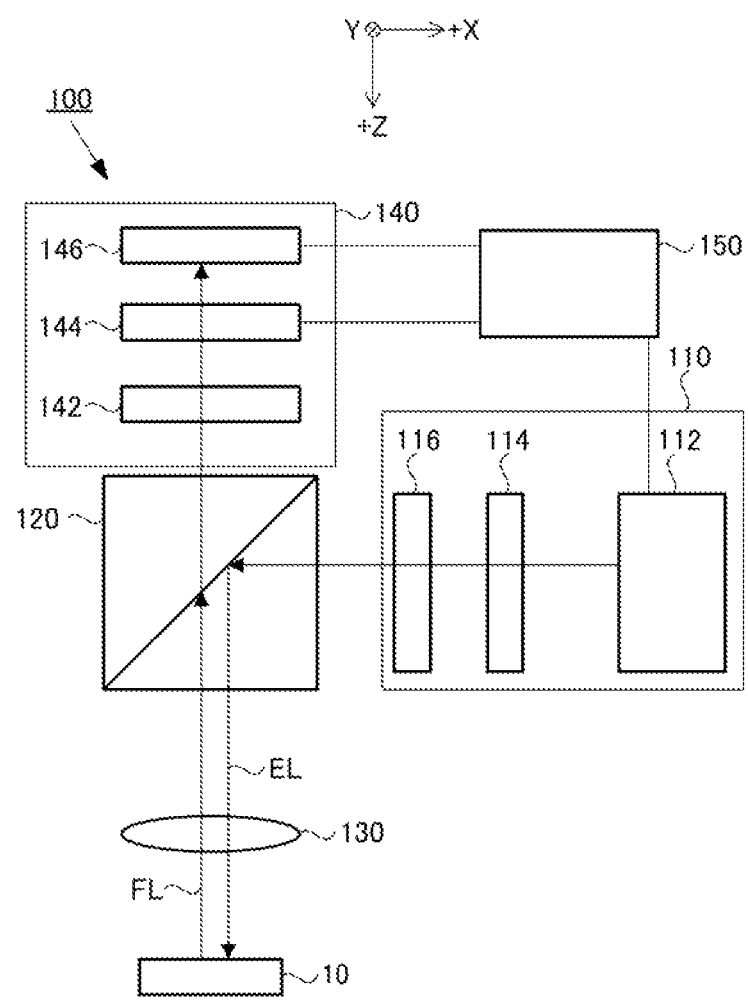
FIG. 8 is a schematic diagram illustrating the analysis device according to Embodiment 1.

As illustrated in FIG. 7 and FIG. 8, the analysis device 100 includes an irradiator 110, a dichroic mirror 120, an object lens 130, a detector 140, and a controller 150. The analysis device 100 further includes the microdevice 10.

The irradiator 110 in the analysis device 100 emits linearly polarized excitation light EL in the −X-direction, as illustrated in FIG. 8. The irradiator 110 includes a light source 112, an excitation light filter 114, a polarization filter 116, and unillustrated optical parts such as a condensing lens, as illustrated in FIG. 7 and FIG. 8. The light source 112 emits light including excitation light EL in the −X-direction. For example, the light source 112 is configured with an LED element. The excitation light filter 114 eliminates light other than the excitation light EL in the light emitted from the light source 112. For example, the excitation light filter 114 is a band-pass filter. The polarization filter 116 converts the excitation light EL passing through the excitation light filter 114 into linearly polarized light.

The dichroic mirror 120 in the analysis device 100 reflects the linearly polarized excitation light EL emitted from the irradiator 110 in a direction toward where the microdevice 10 is placed (+Z-direction), as illustrated in FIG. 8. Further, the dichroic mirror 120 transmits fluorescent light FL emitted from the microdevice 10.

The microdevice 10 in the analysis device 100 is placed on the +Z-side of the dichroic mirror 120 with the first substrate 12 facing in the −Z-direction. The linearly polarized excitation light EL reflected by the dichroic mirror 120 enters the microchannel 18 from the first substrate 12 in the microdevice 10, as illustrated in FIG. 2 and FIG. 3. Further, the microdevice 10 emits fluorescent light FL in the −Z-direction.

The object lens 130 in the analysis device 100 is placed between the dichroic mirror 120 and the microdevice 10, as illustrated in FIG. 8. The object lens 130 condenses the excitation light EL and the fluorescent light FL.

The detector 140 in the analysis device 100 is placed on the −Z-side of the dichroic mirror 120, as illustrated in FIG. 8. The detector 140 detects the fluorescent light FL emitted from the microdevice 10. As illustrated in FIG. 7 and FIG. 8, the detector 140 includes an absorption filter 142, a polarization adjustment element 144, an imaging element 146, and unillustrated optical parts such as an imaging lens. The absorption filter 142 separates the fluorescent light FL emitted from the microdevice 10 from scattered light, leaked light, and the like and transmits the emitted fluorescent light FL. For example, the absorption filter 142 is a band-pass filter. The polarization adjustment element 144 adjusts the polarization direction of the fluorescent light FL transmitted through the absorption filter 142. The polarization adjustment element 144 adjusts the polarization direction of the fluorescent light FL to a direction parallel with the polarization direction of the excitation light EL emitted from the irradiator 110 and a direction perpendicular to the polarization direction of the excitation light EL emitted from the irradiator 110. For example, the polarization adjustment element 144 is a liquid crystal element. The imaging element 146 detects the fluorescent light FL emitted form the polarization adjustment element 144 as an image. For example, the imaging element 146 is a charge coupled device (CCD) image sensor.

The controller 150 in the analysis device 100 controls the irradiator 110 and the detector 140. Further, the controller 150 determines the degree of polarization P of the fluorescent light FL emitted from the microdevice 10, from the image of the fluorescent light FL detected by the imaging element 146. Furthermore, the controller 150 determines the concentration of the measurement target substance Ag1 from the degree of polarization P and a previously generated calibration curve. The controller 150 includes a central processing unit (CPU) 152 executing various types of processing, a read only memory (ROM) 154 storing a program and data, a random access memory (RAM) 156 storing data, and an input-output interface 158 inputting and outputting signals between components. A function of the controller 150 is provided by the CPU 152 executing the program stored in the ROM 154. The input-output interface 158 inputs and outputs signals among the CPU 152, the irradiator 110, and the detector 140.

An operation of the analysis device 100 and detection of the measurement target substance Ag1 will be described.

First, a measurement target solution is introduced to the microchannel 18 in the microdevice 10, and then the microdevice 10 is placed at a predetermined position in the analysis device 100. Next, after a competitive reaction to the antibody Ab1 in the microchannel 18 between the measurement target substance Ag1 and the fluorescence-labeled derivative AgF1 reaches an equilibrium state, linearly polarized excitation light EL is emitted from the irradiator 110 in the analysis device 100, and the irradiation region S in the microdevice 10 is irradiated by the linearly polarized excitation light EL through the dichroic mirror 120 and the object lens 130, as illustrated in FIG. 8.

The linearly polarized excitation light EL enters the microdevice 10 from the first substrate 12, as illustrated in FIG. 3. In this case, the first light blocker 16 blocks the excitation light EL entering the bound fluorescence-labeled derivative AgF1, and therefore fluorescence by the bound fluorescence-labeled derivative AgF1 is suppressed, and fluorescent light FL radiated by the free fluorescence-labeled derivative AgF1 in the microchannel 18 is emitted from the microdevice 10 in the −Z-direction. Since a competitive reaction has reached an equilibrium state, the amount of the free fluorescence-labeled derivative AgF1 in the microchannel 18 is related to the concentration of the measurement target substance Ag1.

The fluorescent light FL emitted from the microdevice 10 enters the detector 140 through the object lens 130 and the dichroic mirror 120, as illustrated in FIG. 8. The detector 140 adjusts the polarization direction of the fluorescent light FL by the polarization adjustment element 144. Then, the detector 140 acquires, by the imaging element 146, an image of fluorescent light FL having a polarization direction parallel with the polarization direction of the excitation light EL and an image of fluorescent light FL having a polarization direction perpendicular to the polarization direction of the excitation light EL.

The controller 150 determines the degree of polarization P of the fluorescent light FL from the acquired images of the fluorescent light FL. Denoting the intensity of the fluorescent light FL having a polarization direction parallel with the polarization direction of the excitation light EL by Ih, and the intensity of the fluorescent light FL having a polarization direction perpendicular to the polarization direction of the excitation light EL by Iv, the degree of polarization P of the fluorescent light FL is represented by $P=(Ih-Iv)/(Ih+Iv)$. Furthermore, the controller 150 determines the concentration of the measurement target substance Ag1 from the degree of polarization P and a previously generated calibration curve. Thus, the concentration of the measurement target substance Ag1 can be acquired.

In the analysis device 100, fluorescence by the bound fluorescence-labeled derivative AgF1 is suppressed, and fluorescent light FL radiated by the free fluorescence-labeled derivative AgF1 is detected. Accordingly, the analysis device 100 can measure the concentration of the measurement target substance Ag1 with high measurement sensitivity.

As described above, in the microdevice 10, the first light blocker 16 blocks excitation light EL entering the bound fluorescence-labeled derivative AgF1, and therefore when a measurement target solution is introduced to the microchannel 18, fluorescence by the bound fluorescence-labeled derivative AgF1 is suppressed, and fluorescent light FL radiated by the free fluorescence-labeled derivative AgF1 is emitted. Accordingly, the microdevice 10 can increase measurement sensitivity to the measurement target substance Ag1. The microdevice 10 can suppress fluorescence by the bound fluorescence-labeled derivative AgF1 and therefore can detect the measurement target substance Ag1 having a higher molecular weight. Furthermore, the microdevice 10 can detect the measurement target substance Ag1 without adding the fluorescence-labeled derivative AgF1 to a measurement target solution and therefore can easily detect the measurement target substance Ag1.

The analysis device 100 suppresses fluorescence by the bound fluorescence-labeled derivative AgF1 and detects fluorescent light FL radiated by the free fluorescence-labeled derivative AgF1. Accordingly, the analysis device 100 can detect a measurement target substance Ag1 with high measurement sensitivity. Further, the analysis device 100 can easily detect the measurement target substance Ag1. Furthermore, the analysis device 100 determines the concentration of the measurement target substance Ag1 from the degree of polarization P and therefore can suppress effects such as scattering of excitation light EL and variation in intensity of light emitted by the light source 112 and can determine the concentration of the measurement target substance Ag1 with high precision.

Embodiment 2

While the first light blocker 16 forms the microchannel 18 in Embodiment 1, another member may form the microchannel 18. Further, a second light blocker 26 blocking excitation light EL may be provided on another member.

Figure 9:
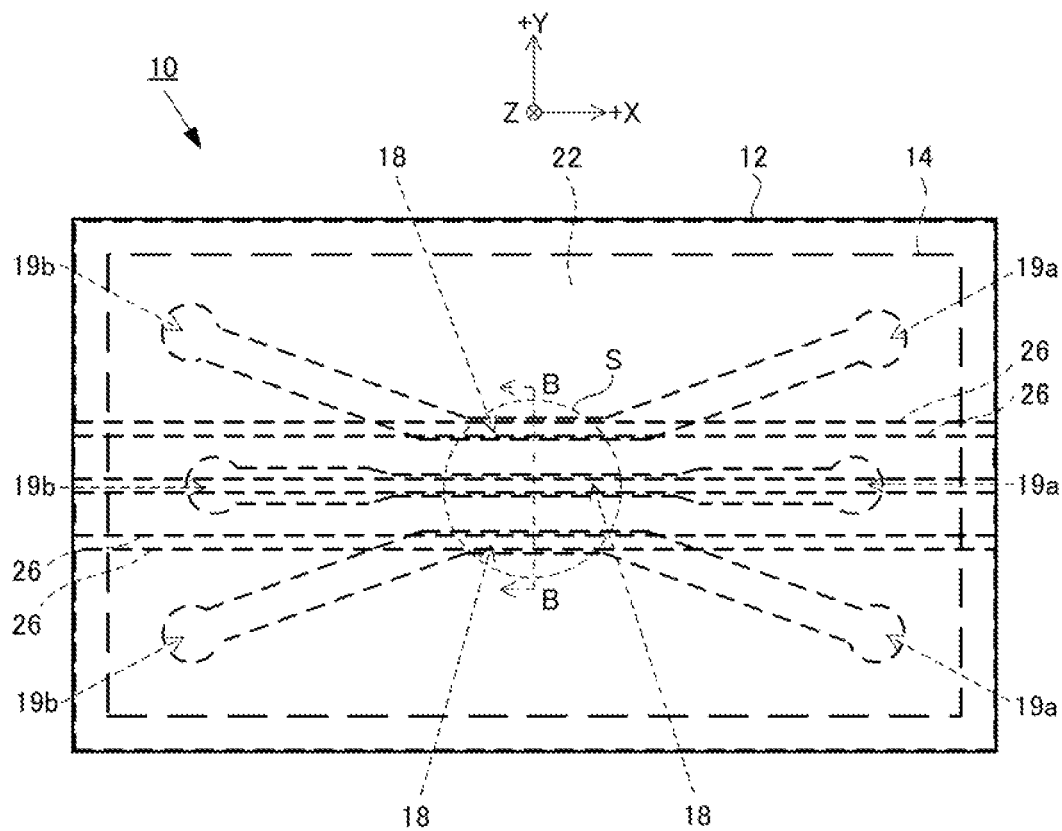
FIG. 9 is a top view illustrating a microdevice according to Embodiment 2.
Figure 10:
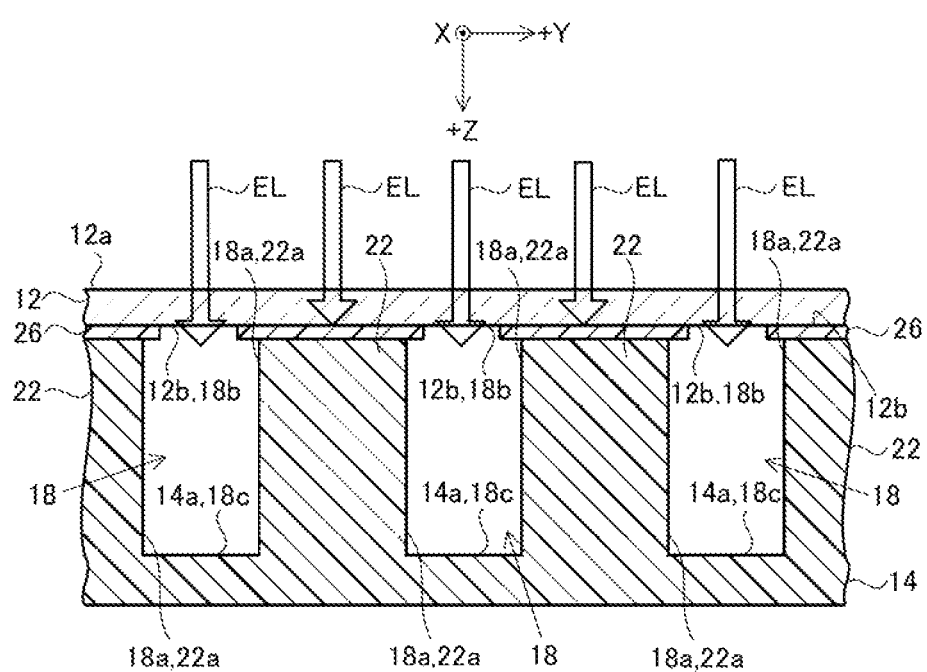
FIG. 10 is a cross-sectional view of the microdevice illustrated in FIG. 9 taken along a line B-B.
Figure 11:
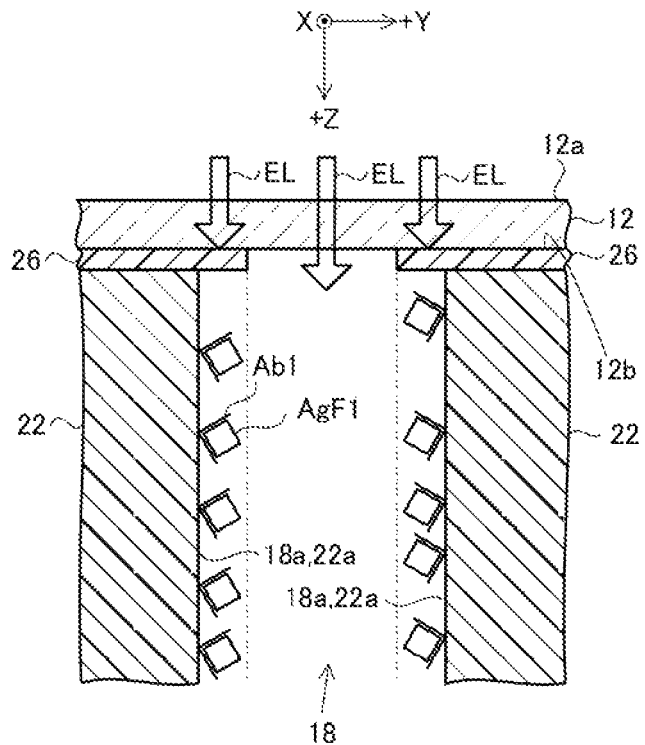
FIG. 11 is a schematic diagram illustrating an antibody and a fluorescence-labeled derivative, according to Embodiment 2.

A microdevice 10 according to the present embodiment will be described with reference to FIG. 9 to FIG. 11. As illustrated in FIG. 9 and FIG. 10, the microdevice 10 according to the present embodiment includes a first substrate 12, a second substrate 14, three microchannels 18, a partition wall 22, and a second light blocker 26. Furthermore, the microdevice 10 according to the present embodiment includes an antibody Ab1 and a fluorescence-labeled derivative AgF1, as illustrated in FIG. 11. In the present embodiment, the partition wall 22 forms the microchannel 18. Further, the second light blocker 26 is provided on the first substrate 12. The second light blocker 26 blocks excitation light EL entering a bound fluorescence-labeled derivative AgF1.

The second light blocker 26 is provided on a second principal plane 12b of the first substrate 12 according to the present embodiment, as illustrated in FIG. 10. The first substrate 12 according to the present embodiment sandwiches the partition wall 22 along with the second substrate 14. The remaining configuration of the first substrate 12 according to the present embodiment is similar to that according to Embodiment 1.

The second substrate 14 according to the present embodiment sandwiches the partition wall 22 along with the first substrate 12. Further, the second substrate 14 according to the present embodiment is integrally formed with the partition wall 22. The remaining configuration of the second substrate 14 according to the present embodiment is similar to that according to Embodiment 1.

The partition wall 22 is sandwiched by the first substrate 12 and the second substrate 14 and forms the microchannel 18. The partition wall 22 is formed of a material with low autofluorescence. Further, the partition wall 22 is preferably formed of a material absorbing light such as excitation light EL and fluorescent light FL. In the present embodiment, the partition wall 22 is integrally formed of polydimethylsiloxane containing carbon black with the second substrate 14.

When viewed at a section of the microchannel 18 in a widthwise direction (YZ plane), a side 22a of the partition wall 22 forms a sidewall surface 18a of the microchannel 18. In the present embodiment, the two sides 22a forming the two sidewall surfaces 18a of the microchannel 18 are perpendicular to the second principal plane 12b of the first substrate 12 and a first principal plane 14a of the second substrate 14. As illustrated in FIG. 11, the antibody Ab1 is fixed to the side 22a of the partition wall 22 (that is, the sidewall surface 18a of the microchannel 18) in a state of specifically binding to the fluorescence-labeled derivative AgF1.

In the microchannel 18 according to the present embodiment, the sidewall surface 18a is formed by the side 22a of the partition wall 22. Further, a section of the microchannel 18 according to the present embodiment in the widthwise direction (Y-direction) has a rectangular shape. The remaining configuration of the microchannel 18 according to the present embodiment is similar to that according to Embodiment 1.

The antibody Ab1 according to the present embodiment is fixed to the sidewall surface 18a of the microchannel 18 (that is, the side 22a of the partition wall 22). Further, the fluorescence-labeled derivative AgF1 according to the present embodiment is specifically bound to the antibody Ab1 by an antigen-antibody reaction. A configuration of the antibody Ab1 and the fluorescence-labeled derivative AgF1 according to the present embodiment is similar to that according to Embodiment 1.

The second light blocker 26 according to the present embodiment is provided on the second principal plane 12b of the first substrate 12 and blocks excitation light EL entering a bound fluorescence-labeled derivative AgF1. For example, the second light blocker 26 according to the present embodiment is formed of resin containing carbon black.

In the microdevice 10 according to the present embodiment, the second light blocker 26 provided on the first substrate 12 blocks excitation light EL entering the bound fluorescence-labeled derivative AgF1, and therefore when a measurement target solution is introduced to the microchannel 18, fluorescence by the bound fluorescence-labeled derivative AgF1 is suppressed, and fluorescent light radiated by a free fluorescence-labeled derivative AgF1 is emitted, similarly to the microdevice 10 according to Embodiment 1. Accordingly, the microdevice 10 according to the present embodiment can improve measurement sensitivity to a measurement target substance Ag1, similarly to the microdevice 10 according to Embodiment 1. Further, the microdevice 10 according to the present embodiment can detect the measurement target substance Ag1 having a higher molecular weight. Furthermore, the microdevice 10 according to the present embodiment can easily detect the measurement target substance Ag1, similarly to the microdevice 10 according to Embodiment 1.

Embodiment 3

While one antibody Ab1 is fixed to the microchannel 18 in Embodiment 1 and Embodiment 2, a plurality of antibodies Ab1, Ab2, and Ab3 may be fixed to one microchannel 18.

Figure 12:
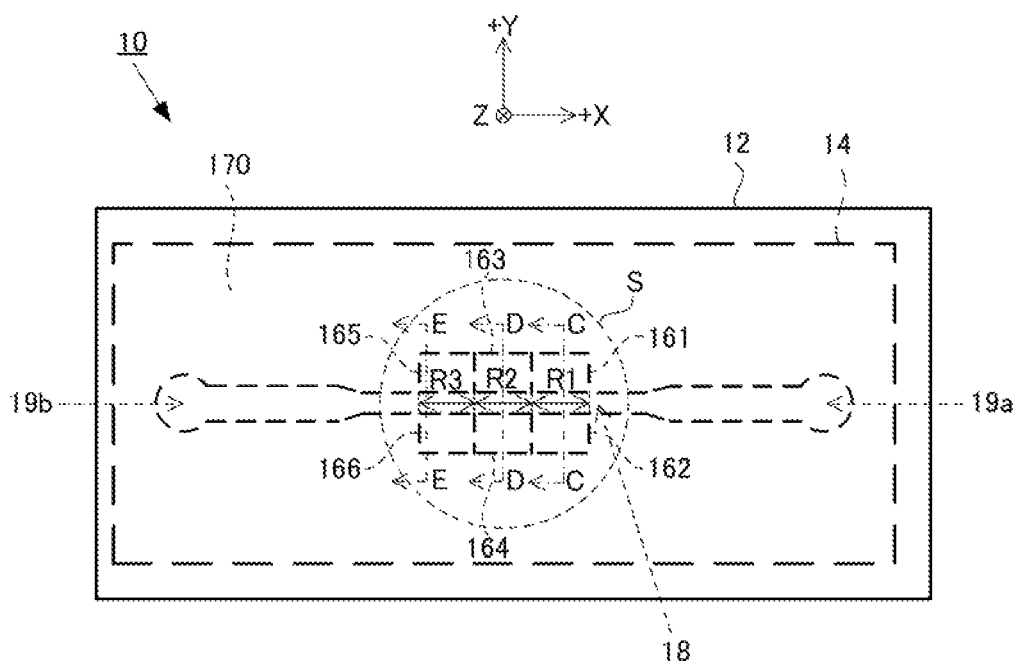
FIG. 12 is a top view illustrating a microdevice according to Embodiment 3.
Figure 13:
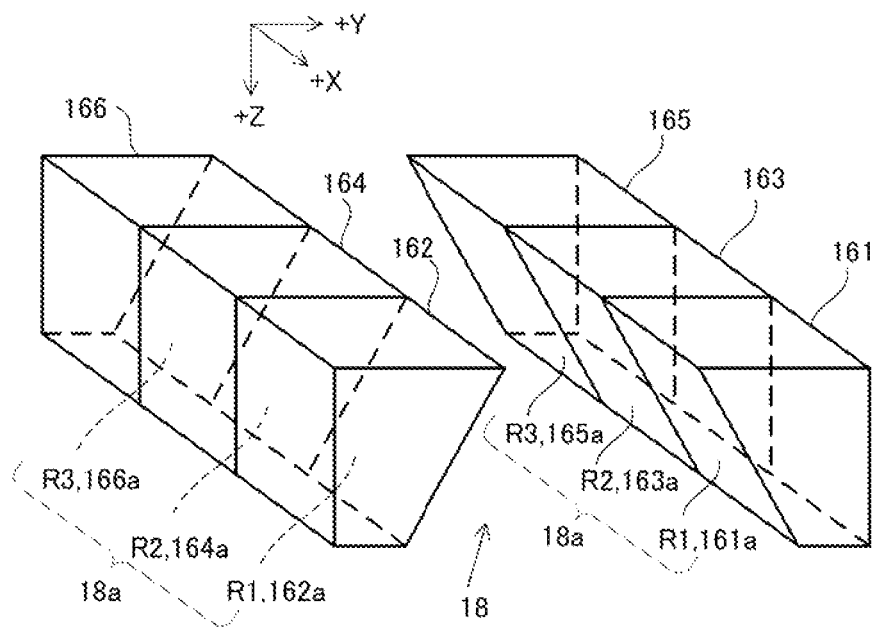
FIG. 13 is a schematic diagram illustrating a sidewall surface of a microchannel in an irradiation region according to Embodiment 3.
Figure 14:
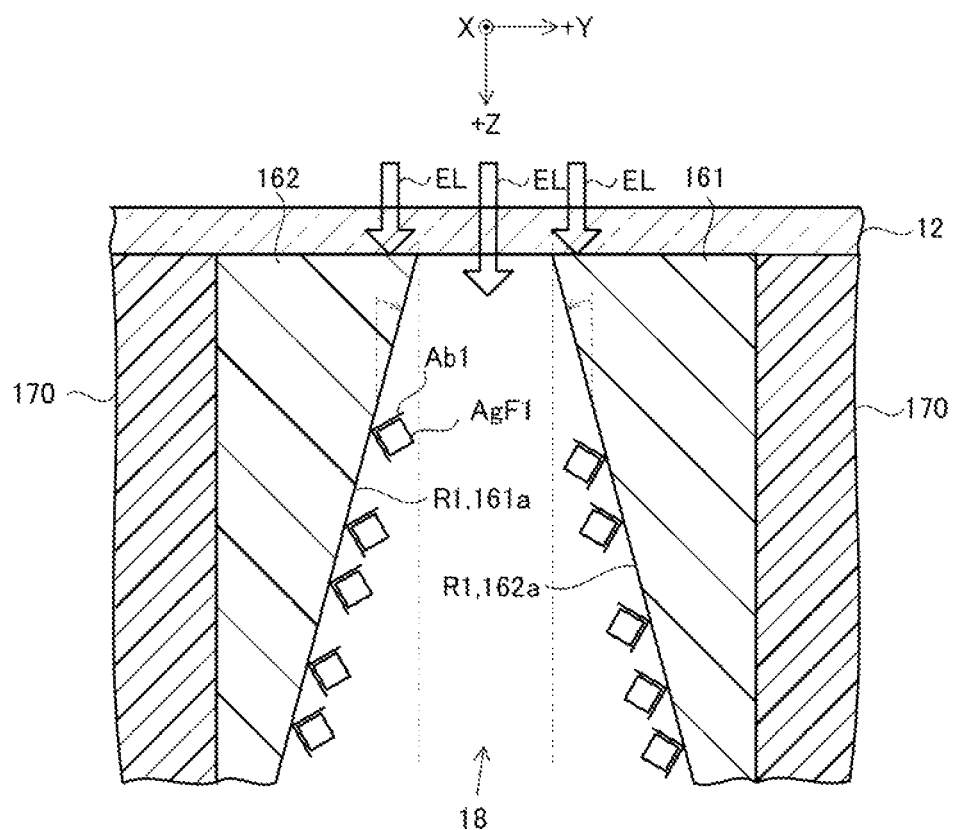
FIG. 14 is a cross-sectional view of the microdevice illustrated in FIG. 12 taken along a line C-C.
Figure 15:
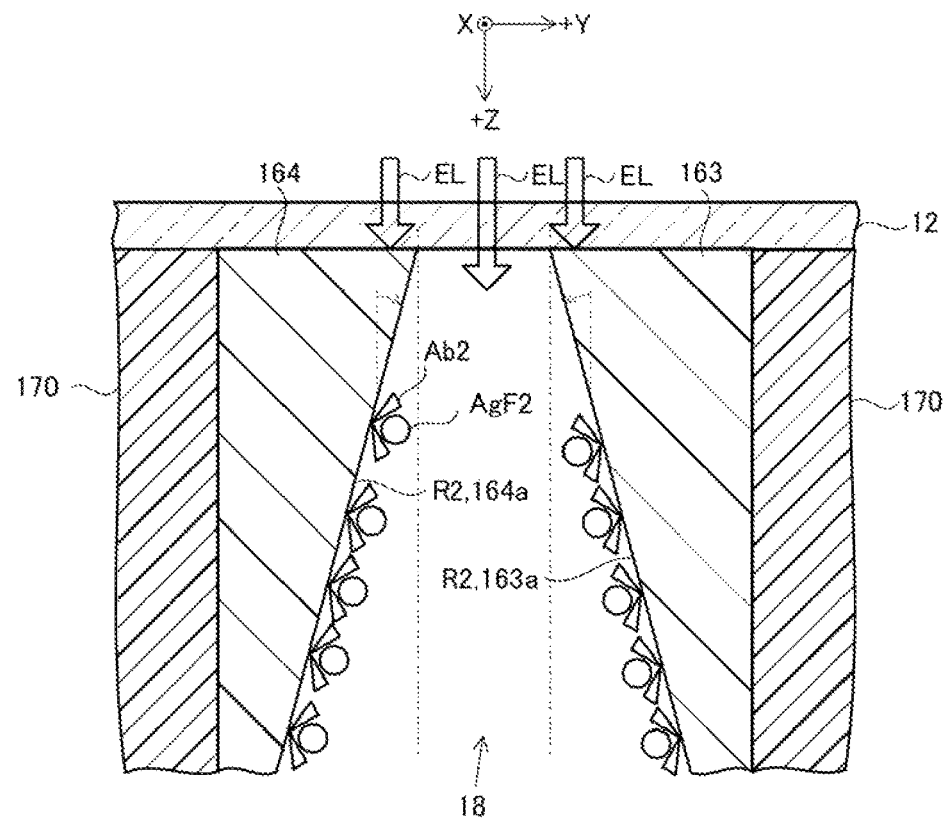
FIG. 15 is a cross-sectional view of the microdevice illustrated in FIG. 12 taken along a line D-D.
Figure 16:
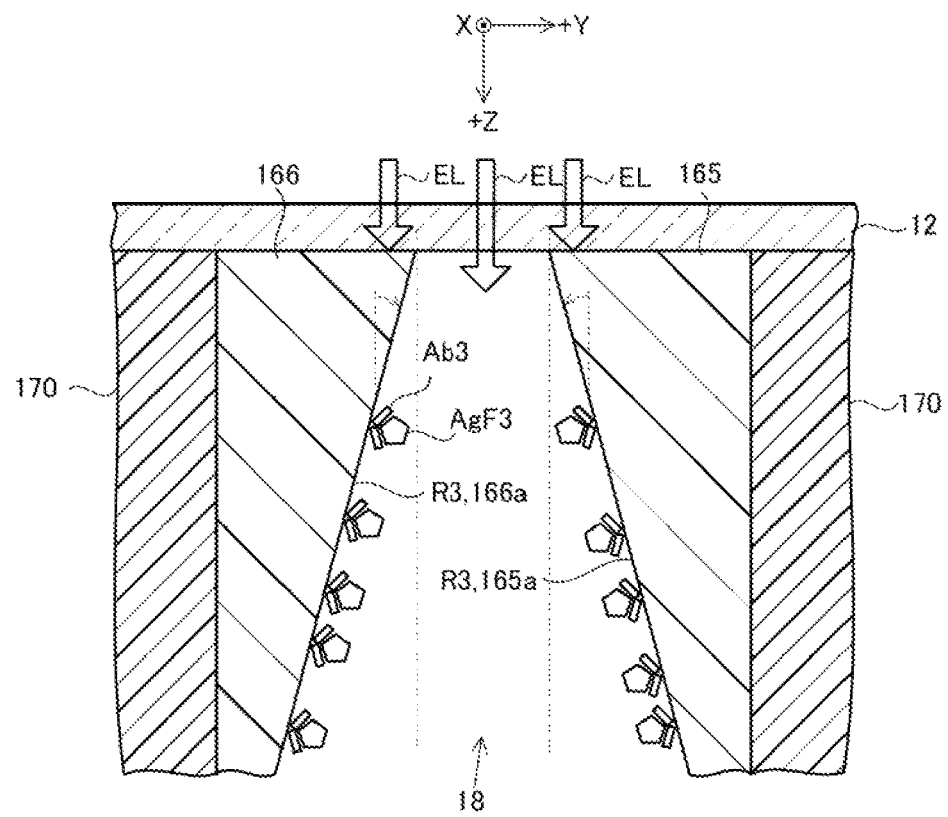
FIG. 16 is a cross-sectional view of the microdevice illustrated in FIG. 12 taken along a line E-E.

A microdevice 10 according to the present embodiment will be described with reference to FIG. 12 to FIG. 19. As illustrated in FIG. 12, the microdevice 10 according to the present embodiment includes one microchannel 18. In the present embodiment, a first substrate 12, a second substrate 14, third light blockers 161 to 166, and a fourth light blocker 170 form one microchannel 18. The microchannel 18 in an irradiation region S includes three divisions R1, R2, and R3 along a lengthwise direction (-X-direction). Further, as illustrated in FIG. 13, a sidewall surface 18a of the microchannel 18 in the irradiation region S is divided into divisions R1, R2, and R3 corresponding to the divisions R1, R2, and R3 of the microchannel 18 along the lengthwise direction of the microchannel 18. Furthermore, as illustrated in FIG. 14 to FIG. 16, antibodies Ab1, Ab2, and Ab3 are immobilized in the divisions R1, R2, and R3 of the sidewall surface 18a, respectively, and specifically bind to fluorescence-labeled derivatives AgF1, AgF2, and AgF3, respectively. The remaining configuration is similar to that according to Embodiment 1. The configuration of the microdevice 10 according to the present embodiment will be specifically described below.

In the present embodiment, the third light blockers 161 to 166 and the fourth light blocker 170 are sandwiched by the first substrate 12 and the second substrate 14 and form the microchannel 18. The third light blockers 161 to 166 form the microchannel 18 in the irradiation region S, as illustrated in FIG. 12. Each of the third light blockers 161 to 166 has a quadrangular prism shape the undersurface of which (a section of the microchannel 18 in a widthwise direction) being a rectangular trapezoid, as illustrated in FIG. 13. The third light blockers 161, 163, and 165 are arranged in an X-direction, and respective inclining sides 161a, 163a, and 165a of the third light blockers 161, 163, and 165 form one sidewall surface 18a of the microchannel 18. The third light blockers 162, 164, and 166 are arranged in the X-direction, and respective inclining sides 162a, 164a, and 166a of the third light blockers 162, 164, and 166 form the other sidewall surface 18a of the microchannel 18.

Furthermore, as illustrated in FIG. 13 to FIG. 16, the third light blocker 161 and the third light blocker 162 face each other, and the side 161a of the third light blocker 161 and the side 162a of the third light blocker 162 form the division R1 of the two sidewall surfaces 18a. Similarly to the third light blocker 161 and the third light blocker 162, the side 163a of the third light blocker 163 and the side 164a of the third light blocker 164 form the division R2 of the sidewall surfaces 18a, and the side 165a of the third light blocker 165 and the side 166a of the third light blocker 166 form the division R3 of the sidewall surfaces 18a.

Figure 17:
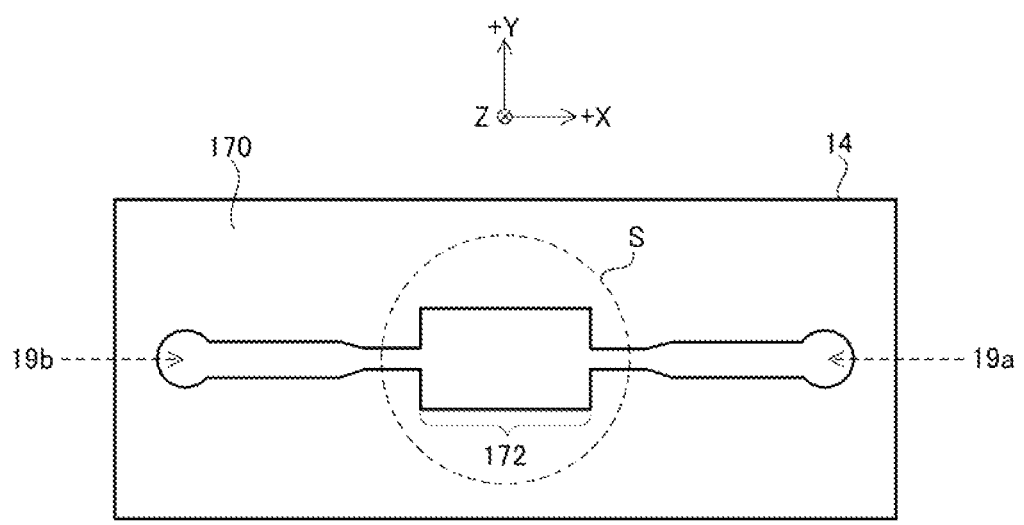
FIG. 17 is a top view illustrating a fourth light blocker and a second substrate, according to Embodiment 3.

The fourth light blocker 170 forms the microchannel 18 other than the microchannel 18 formed by the third light blockers 161 to 166. The fourth light blocker 170 includes a groove 172 into which the third light blockers 161 to 166 are fitted, as illustrated in FIG. 17. In the present embodiment, the fourth light blocker 170 is integrally formed with the second substrate 14.

In the present embodiment, the antibody Ab1 is fixed to the division R1 of the sidewall surface 18a in a state of binding to the fluorescence-labeled derivative AgF1 acquired by fluorescence-labeling a measurement target substance Ag1. The measurement target substance Ag1 and the fluorescence-labeled derivative AgF1 specifically bind to the antibody Ab1 and bind to neither the antibody Ab2 nor the antibody Ab3. Further, the antibody Ab2 is fixed to the division R2 of the sidewall surface 18a in a state of binding to the fluorescence-labeled derivative AgF2 acquired by fluorescence-labeling a measurement target substance Ag2. The measurement target substance Ag2 and the fluorescence-labeled derivative AgF2 specifically bind to the antibody Ab2 and bind to neither the antibody Ab1 nor the antibody Ab3. Furthermore, the antibody Ab3 is fixed to the division R3 of the sidewall surface 18a in a state of binding to the fluorescence-labeled derivative AgF3 acquired by fluorescence-labeling a measurement target substance Ag3. The measurement target substance Ag3 and the fluorescence-labeled derivative AgF3 specifically bind to the antibody Ab3 and bind to neither the antibody Ab1 nor the antibody Ab2.

In the present embodiment, the sides 161a to 166a of the third light blockers 161 to 166 (the sidewall surfaces 18a of the microchannel 18) incline in a direction narrowing the width of the microchannel 18 toward the first substrate 12, similarly to the sides 16a of the first light blocker 16 according to Embodiment 1. Accordingly, the third light blockers 161 to 166 block excitation light EL entering bound fluorescence-labeled derivatives AgF1, AgF2, and AgF3, similarly to the first light blocker 16 according to Embodiment 1, and even when the microdevice 10 is irradiated by excitation light EL, the bound fluorescence-labeled derivatives AgF1, AgF2, and AgF3 do not radiate fluorescent light, similarly to the bound fluorescence-labeled derivative AgF1 according to Embodiment 1.

Next, an operation of the microdevice 10 according to the present embodiment will be described.

When a measurement target solution containing the measurement target substances Ag1, Ag2, and Ag3 is introduced to the microchannel 18 in the microdevice 10, the measurement target substance Ag1 specifically bind to the antibody Ab1 by an antigen-antibody reaction in competition with the fluorescence-labeled derivative AgF1, in the division R1 of the sidewall surface 18a. Then, a free fluorescence-labeled derivative AgF1 is produced in the division R1 of the microchannel 18. Further, a free fluorescence-labeled derivative AgF2 is produced in the division R2 of the microchannel 18, and a free fluorescence-labeled derivative AgF3 is produced in the division R3 of the microchannel 18, similarly to the free fluorescence-labeled derivative AgF1.

When the competitive reaction reaches an equilibrium state, the free fluorescence-labeled derivatives AgF1, AgF2, and AgF3 with amounts according to the concentrations of the measurement target substances Ag1, Ag2, and Ag3 are produced. When excitation light EL enters the first substrate 12 after the competitive reaction reaches the equilibrium state, the third light blockers 161 to 166 block the excitation light EL entering the bound fluorescence-labeled derivatives AgF1, AgF2, and AgF3, and therefore fluorescent light radiated by the free fluorescence-labeled derivatives AgF1, AgF2, and AgF3 is measured. Accordingly, the concentrations of the measurement target substances Ag1, Ag2, and Ag3 can be determined from the degrees of polarization P of the divisions R1, R2, and R3 of the microchannel 18. Further, the microdevice 10 according to the present embodiment can improve measurement sensitivity to the measurement target substances Ag1, Ag2, and Ag3, similarly to the microdevice 10 according to Embodiment 1.

Figure 18:
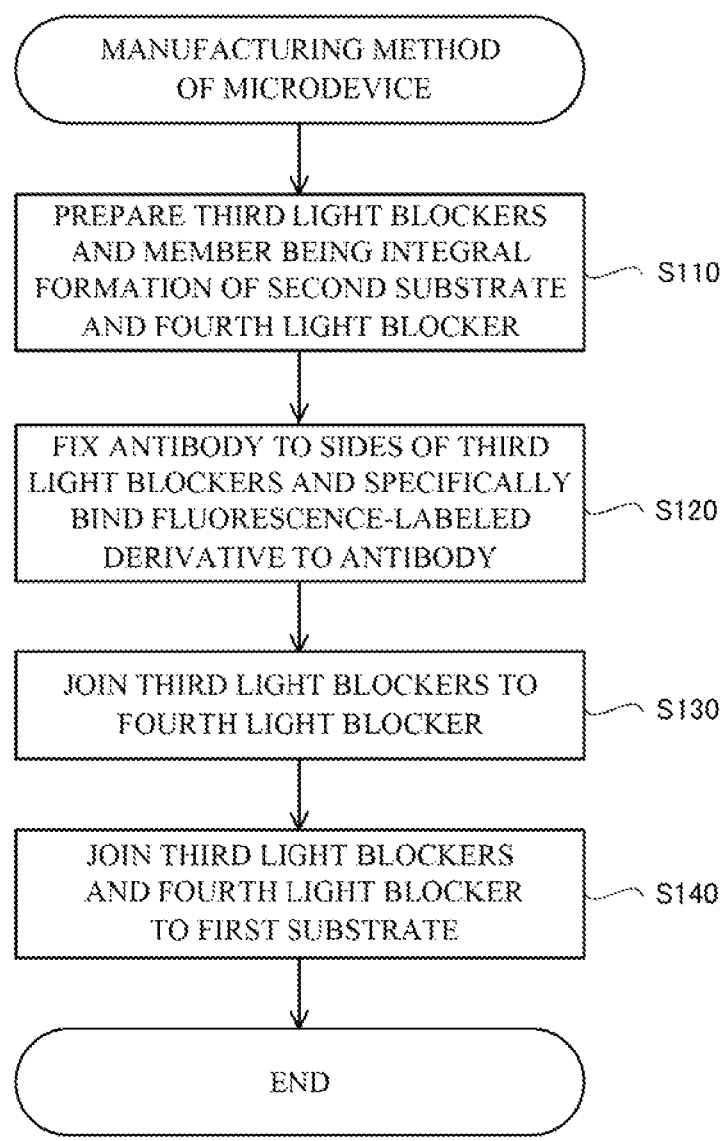
FIG. 18 is a flowchart illustrating a manufacturing method of the microdevice according to Embodiment 3.
Figure 19:
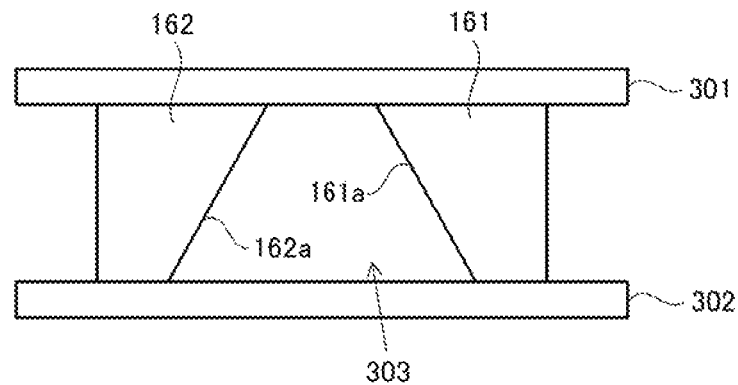
FIG. 19 is a schematic diagram for illustrating a process of fixing an antibody to a side of a third light blocker and specifically binding a fluorescence-labeled derivative to the fixed antibody, according to Embodiment 3.

Next, a manufacturing method of the microdevice 10 according to the present embodiment will be described with reference to FIG. 18 and FIG. 19. FIG. 18 is a flowchart illustrating the manufacturing method of the microdevice 10 according to the present embodiment. For ease of understanding, the antibodies Ab1, Ab2, and Ab3 may be hereinafter generically described as antibodies Ab, and the fluorescence-labeled derivatives AgF1, AgF2, and AgF3 may be generically described as fluorescence-labeled derivatives AgF.

The manufacturing method of the microdevice 10 according to the present embodiment includes a process of preparing the third light blockers 161 to 166 and a member being an integral formation of the second substrate 14 and the fourth light blocker 170 (Step S110), a process of fixing the antibody Ab to the sides 161a to 166a of the third light blockers 161 to 166 and specifically binding the fluorescence-labeled derivative AgF to the fixed antibody Ab (Step S120), a process of joining the third light blockers 161 to 166 to the fourth light blocker 170 (Step S130), and a process of joining the third light blockers 161 to 166 and the fourth light blocker 170 to the first substrate 12 (Step S140).

In Step S110, the third light blockers 161 to 166 are prepared. The third light blockers 161 to 166 are cut out of a block of polydimethylsiloxane resin containing carbon black. Further, a member being an integral formation of the second substrate 14 and the fourth light blocker 170 is prepared. The member being an integral formation of the second substrate 14 and the fourth light blocker 170 is formed by using a mold, similarly to Step S10 according to Embodiment 1. Furthermore, an inlet 19a and an outlet 19b are formed by using a jig, similarly to Step S20 according to Embodiment 1.

Step S120 will be described with the third light blocker 161 and the third light blocker 162 as an example. First, a channel 303 with the side 161a of the third light blocker 161 and the side 162a of the third light blocker 162 as sidewall surfaces is formed by sandwiching the third light blocker 161 and the third light blocker 162 by two glass substrates 301 and 302, as illustrated in FIG. 19. Next, a solution containing the antibody Ab1 is introduced to the formed channel 303, and the antibody Ab1 is fixed to the side 161a of the third light blocker 161 and the side 162a of the third light blocker 162. Next, a solution containing the fluorescence-labeled derivative AgF1 is introduced to the channel 303, and the fluorescence-labeled derivative AgF1 is bound to the antibody Ab1 by an antigen-antibody reaction. Thus, the antibody Ab1 can be fixed to the side 161a and the side 162a, and the fluorescence-labeled derivative AgF1 can be specifically bound to the antibody Ab1. With respect to the third light blocker 163 and the third light blocker 164, the antibody Ab2 is fixed, and the fluorescence-labeled derivative AgF2 is specifically bound to the antibody Ab2, similarly to the third light blocker 161 and the third light blocker 162. Further, with respect to the third light blocker 165 and the third light blocker 166, the antibody Ab3 is fixed, and the fluorescence-labeled derivative AgF3 is specifically bound to the antibody Ab3, similarly to the third light blocker 161 and the third light blocker 162.

In Step S130, first, the third light blockers 161 to 166 are placed in the groove 172 of the fourth light blocker 170. Next, by pressing the third light blockers 161 to 166 and the fourth light blocker 170 against each other, the third light blockers 161 to 166 are joined to the fourth light blocker 170. Consequently, the sidewall surfaces 18a of the microchannel 18 including the divisions R1, R2, and R3 are formed.

In Step S140, first, the first substrate 12 is placed on the third light blockers 161 to 166 and the fourth light blocker 170. Then, by pressing the first substrate 12 against the third light blockers 161 to 166 and the fourth light blocker 170, the third light blockers 161 to 166 and the fourth light blocker 170 are joined to the first substrate 12. Thus, the microdevice 10 according to the present embodiment can be produced.

As described above, in the present embodiment, the third light blockers 161 to 166 block excitation light EL entering the bound fluorescence-labeled derivatives AgF1, AgF2, and AgF3, and therefore when a measurement target solution is introduced to the microchannel 18, fluorescence by the bound fluorescence-labeled derivatives AgF1, AgF2, and AgF3 is suppressed. Accordingly, the microdevice 10 can increase measurement sensitivity to the measurement target substances Ag1, Ag2, and Ag3, similarly to the microdevice 10 according to Embodiment 1. Further, the sidewall surface 18a of the microchannel 18 in the irradiation region S is divided into a plurality of divisions R1, R2, and R3 along the lengthwise direction of the microchannel 18, and a plurality of antibodies Ab1, Ab2, and Ab3 is fixed for respective divisions; and therefore a plurality of measurement target substances Ag1, Ag2, and Ag3 can be detected. The microdevice 10 according to the present embodiment can easily detect the measurement target substances Ag1, Ag2, and Ag3, similarly to the microdevice 10 according to Embodiment 1. Furthermore, the microdevice 10 according to the present embodiment can detect measurement target substances Ag1, Ag2, and Ag3 having higher molecular weights.

Embodiment 4

While the antibody Ab is fixed to the sidewall surface 18a in a state of specifically binding to the fluorescence-labeled derivative AgF in Embodiment 1 to Embodiment 3, the antibody Ab may not bind to the fluorescence-labeled derivative AgF.

Figure 20:
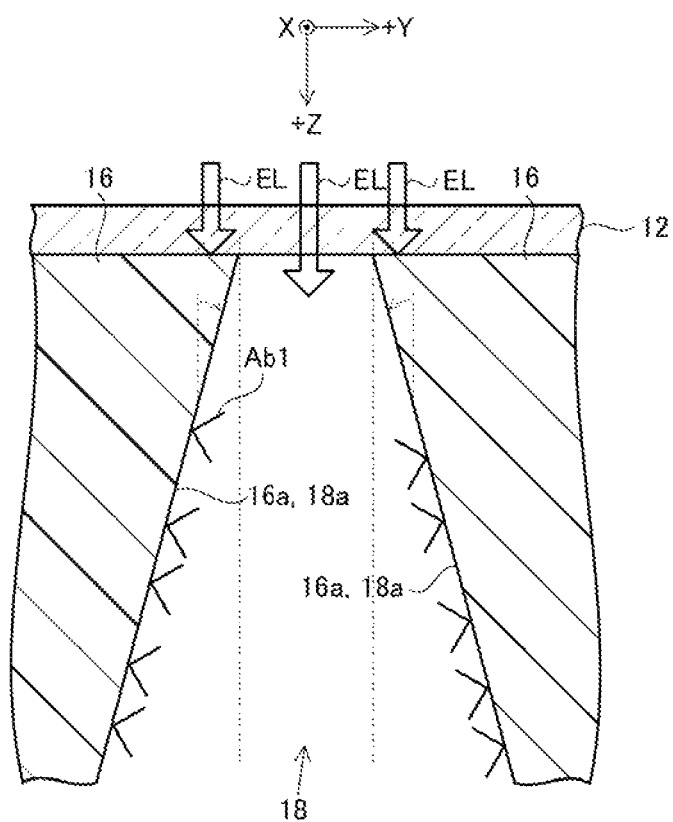
FIG. 20 is a schematic diagram illustrating an antibody according to Embodiment 4.

In a microdevice 10 according to the present embodiment, an antibody Ab1 fixed to a sidewall surface 18a is not specifically binding to a fluorescence-labeled derivative AgF1, as illustrated in FIG. 20. The remaining configuration of the microdevice 10 according to the present embodiment is similar to that of the microdevice 10 according to Embodiment 1.

In the microdevice 10 according to the present embodiment, a measurement target solution containing a measurement target substance Ag1 and the fluorescence-labeled derivative AgF1 with a predetermined concentration (hereinafter described as a measurement target solution) is introduced to a microchannel 18. When the measurement target solution is introduced to the microchannel 18, the measurement target substance Ag1 and the fluorescence-labeled derivative AgF1 cause antigen-antibody reactions to the antibody Ab1 in a competitive manner. When the competitive reaction to the antibody Ab1 between the measurement target substance Ag1 and the fluorescence-labeled derivative AgF1 reaches an equilibrium state, a free fluorescence-labeled derivative AgF1 in an amount according to the concentration of the measurement target substance Ag1 is produced in the microchannel 18, similarly to Embodiment 1.

In the microdevice 10 according to the present embodiment, a first light blocker 16 blocks excitation light EL entering a bound fluorescence-labeled derivative AgF1, similarly to the microdevice 10 according to Embodiment 1. Accordingly, the microdevice 10 according to the present embodiment can suppress fluorescence by the bound fluorescence-labeled derivative AgF1 and improve measurement sensitivity to the measurement target substance Ag1. The microdevice 10 according to the present embodiment can detect a measurement target substance Ag1 having a higher molecular weight.

Modified Example

While the embodiments have been described above, various modifications can be made to the present disclosure without departing from the spirit thereof.

While the second substrate 14 and the first light blocker 16 are integrally formed in Embodiment 1, the second substrate 14 and the first light blocker 16 may be separately formed. Further, the second substrate 14 may transmit excitation light EL.

The second substrate 14, the first light blocker 16, the partition wall 22, the third light blockers 161 to 166, and the fourth light blocker 170 are formed of polydimethylsiloxane containing carbon black but may be formed of another material. For example, polydimethylsiloxane may contain ferric oxide in place of carbon black. Further, the first light blocker 16, the third light blockers 161 to 166, and the like may be formed of polymethyl methacrylate containing ferric oxide.

In the microdevice 10 according to Embodiment 1, the antibody Ab1 is fixed to both sidewall surfaces 18a of the microchannel 18 in a state of specifically binding to the fluorescence-labeled derivative AgF1. The antibody Ab1 according to Embodiment 1 has only to be fixed to at least one of the sidewall surfaces 18a of the microchannel 18 in a state of specifically binding to the fluorescence-labeled derivative AgF1. When the antibody Ab1 is fixed to one of the sidewall surfaces 18a, only the sidewall surface 18a to which the antibody Ab1 is fixed needs to incline in a direction narrowing the width of the microchannel 18 toward the first substrate 12.

Each of a plurality of antibodies Ab may be fixed to the sidewall surface 18a of the microchannel 18 according to Embodiment 1 for each division, similarly to Embodiment 3.

Figure 21:
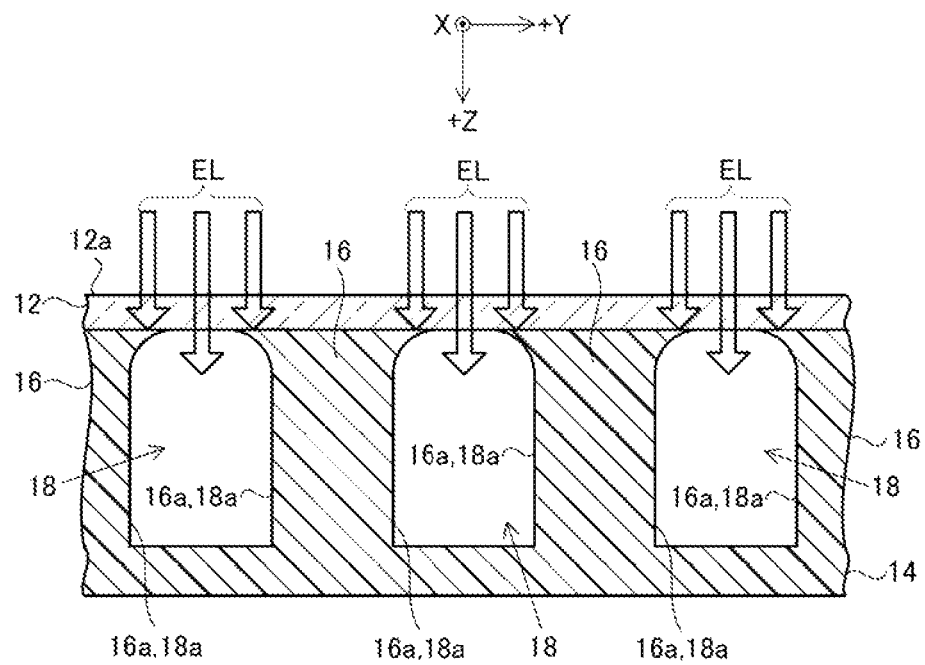
FIG. 21 is a schematic diagram illustrating a section of a microdevice according to a modified example.
Figure 22:
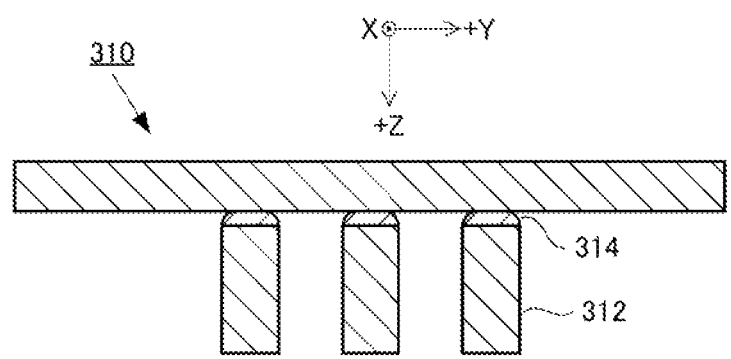
FIG. 22 is a schematic diagram illustrating a section of a mold according to the modified example.

In Embodiment 1, the entire sidewall surface 18a of the microchannel 18 incline in a direction narrowing the width of the microchannel 18 toward the first substrate 12. Part of the sidewall surface 18a according to Embodiment 1 may incline in a direction narrowing the width of the microchannel 18. For example, an end of the sidewall surface 18a on the first substrate 12 side may be warped toward the inside of the microchannel 18, as illustrated in FIG. 21. In this case, for example, the second substrate 14 and the first light blocker 16 are formed by using a mold 310 illustrated in FIG. 22. For example, the mold 310 is produced by performing etching and oxidation treatment on a silicon layer 312 in a silicon on insulator (SOI) substrate and then performing wet etching on the formed oxide film and a silicon oxide film layer 314 in the SOI substrate.

The analysis device 100 may include one of the microdevices 10 according to Embodiment 2 to Embodiment 4 in place of the microdevice 10 according to Embodiment 1. Further, the analysis device 100 may determine the concentration of the measurement target substance Ag1 from the intensity of fluorescent light FL. For example, the analysis device 100 may detect the intensity Iv of fluorescent light FL having a polarization direction perpendicular to the polarization direction of excitation light EL by the detector and determine the concentration of the measurement target substance Ag1 from Iv. Consequently, the S/N ratio of the fluorescent light improves, and measurement sensitivity improves. Furthermore, the imaging element 146 in the detector 140 is not limited to a CCD image sensor. For example, the imaging element 146 in the detector 140 may be a complementary metal oxide semiconductor (CMOS) image sensor.

Figure 23:
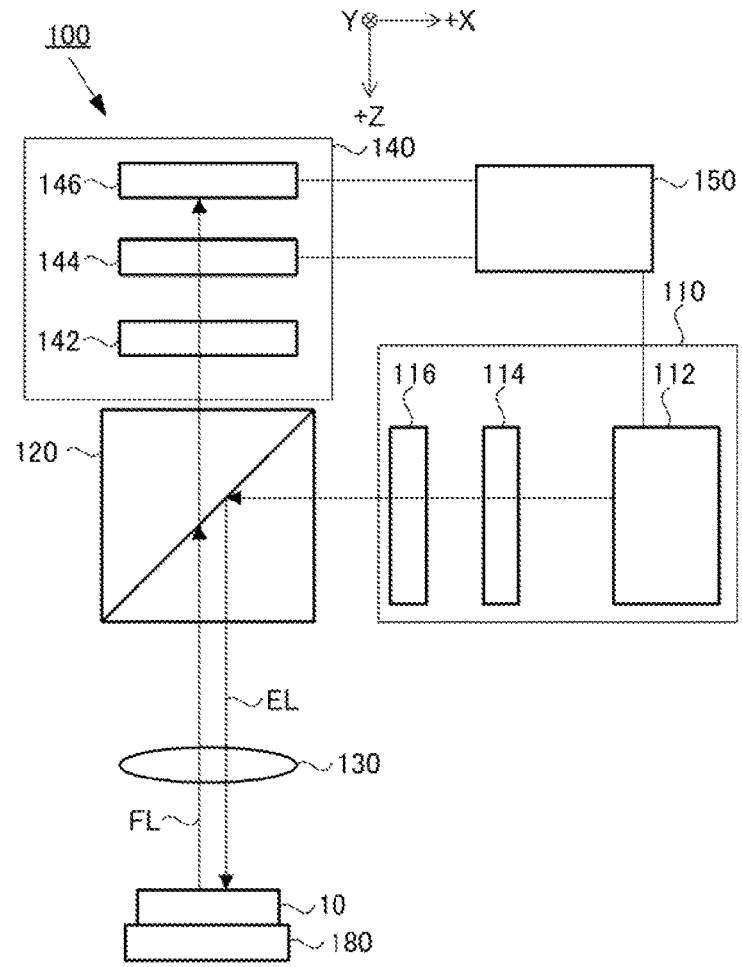
FIG. 23 is a schematic diagram illustrating an analysis device according to a modified example.

The analysis device 100 may include a promotor 180, as illustrated in FIG. 23. The promotor 180 promotes a competitive reaction to the antibody Ab between the measurement target substance Ag and the fluorescence-labeled derivative AgF. Examples of the promotor 180 include a heater heating the microdevice 10 and an ultrasonic device irradiating the microdevice 10 with ultrasonic waves.

While the second substrate 14 and the partition wall 22 are integrally formed in Embodiment 2, the second substrate 14 and the partition wall 22 may be separately formed. Further, the second substrate 14 and the partition wall 22 may transmit excitation light EL.

In Embodiment 2, when viewed at a section of the microchannel 18 in the widthwise direction (YZ plane), the side 22a of the partition wall 22 does not need to be perpendicular to the second principal plane 12b of the first substrate 12 or the first principal plane 14a of the second substrate 14. When viewed at a section of the microchannel 18 in the widthwise direction (YZ plane), the microchannel 18 may have a tapered shape.

Each of a plurality of antibodies Ab may be fixed to the sidewall surface 18a of the microchannel 18 according to Embodiment 2 for each division, similarly to Embodiment 3. Furthermore, the antibody Ab not specifically binding to the fluorescence-labeled derivative AgF may be fixed to the sidewall surface 18a of the microchannel 18 according to Embodiment 2, similarly to Embodiment 4.

Figure 24:
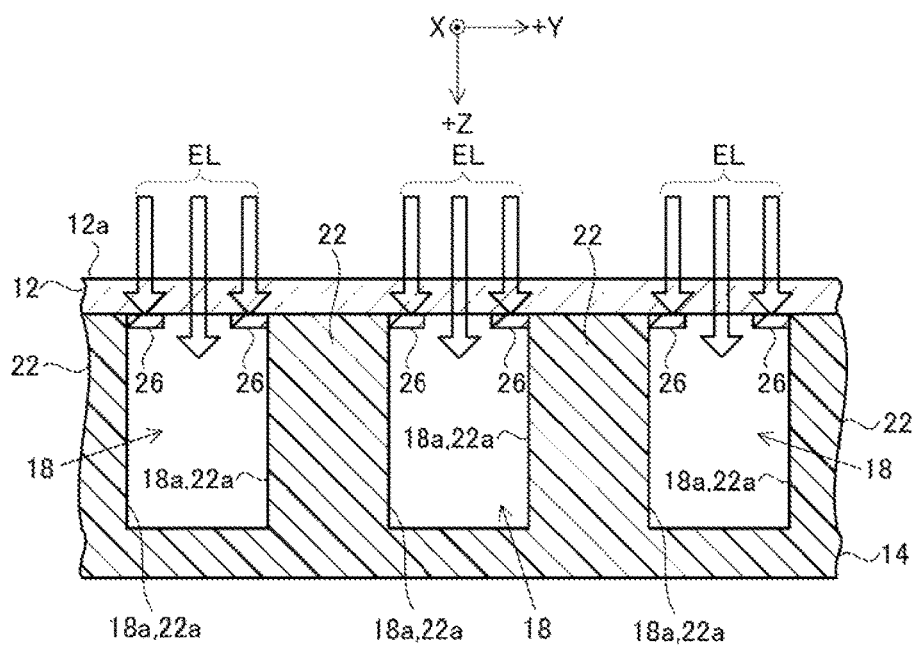
FIG. 24 is a schematic diagram illustrating a section of a microdevice according to a modified example.

While the second light blocker 26 is provided on the second principal plane 12b of the first substrate 12 in Embodiment 2, the second light blocker 26 blocking excitation light EL entering the bound fluorescence-labeled derivative AgF1 may be provided on the partition wall 22. For example, the second light blocker 26 may be provided at an end of the partition wall 22 on the first substrate 12 side, as illustrated in FIG. 24. In this case, the partition wall 22 and the second light blocker 26 may be integrally formed.

The microdevice 10 according to Embodiment 3 may include a plurality of microchannels 18. Further, the number of divisions of the microchannel 18 is not limited to three and has only to be more than one.

In each of the microdevices 10 according to Embodiment 1 to Embodiment 3, the antibody Ab specifically binding to the fluorescence-labeled derivative AgF may be fixed to at least one of the upper wall surface 18b and the lower wall surface 18c of the microchannel 18. The surface area of each of the upper wall surface 18b and the lower wall surface 18c is small compared with the sidewall surface 18a, and therefore even when the antibody Ab specifically binding to the fluorescence-labeled derivative AgF is fixed to at least one of the upper wall surface 18b and the lower wall surface 18c of the microchannel 18, detection of the measurement target substance Ag is hardly affected. The antibody Ab may be fixed to at least one of the upper wall surface 18b and the lower wall surface 18c of the microchannel 18 in the microdevice 10 according to Embodiment 4 as well.

In manufacture of the microdevice 10, for example, the antibody Ab or the antibody Ab specifically binding to the fluorescence-labeled derivative AgF can be fixed to only the sidewall surface 18a by fixing the antibody Ab to the sidewall surface 18a, the upper wall surface 18b, and the lower wall surface 18c and then eliminating the antibody Ab from the upper wall surface 18b and the lower wall surface 18c by irradiating the antibody Ab fixed to the upper wall surface 18b and the lower wall surface 18c with laser light.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

What is claimed is:

1. A microdevice comprising:
    a microchannel to which a measurement target solution containing a measurement target substance is introduced;
    an antibody being fixed to at least one sidewall surface of the microchannel and specifically binding to the measurement target substance;
    a fluorescence-labeled derivative being specifically bound to the antibody and being acquired by fluorescence-labeling the measurement target substance;
    a light blocker blocking excitation light exciting fluorescent light radiated by the fluorescence-labeled derivative; and
    a first substrate that the excitation light enters, wherein
    the measurement target substance and the fluorescence-labeled derivative specifically bind to the antibody in a competitive manner,
    the antibody is fixed to the sidewall surface of the microchannel in a state of specifically binding to the fluorescence-labeled derivative, the light blocker blocks the excitation light entering the fluorescence-labeled derivative specifically binding to the antibody, and
    the light blocker is formed of a material absorbing the excitation light and the fluorescent light,
    wherein a section of the microchannel in a widthwise direction has a tapered shape narrowing toward the first substrate, and
    wherein the light blocker is formed of:
        (i) polydimethylsiloxane containing carbon black or ferric oxide, or
        (ii) polymethyl methacrylate containing carbon black or ferric oxide.

2. The microdevice according to claim 1, wherein
    the antibody is a plurality of antibodies,
    the fluorescence-labeled derivative is a plurality of fluorescence-labeled derivatives,
    the measurement target solution includes a plurality of measurement target substances, and
    each antibody of the plurality of antibodies specifically binds to one measurement target substance out of the plurality of measurement target substances and one fluorescence-labeled derivative out of the plurality of fluorescence-labeled derivatives and is immobilized for each division of the sidewall surface along a lengthwise direction of the microchannel.

3. The microdevice according to claim 1, further comprising:
    a second substrate facing the first substrate, wherein
    the light blocker forms the microchannel by being sandwiched by the first substrate and the second substrate,
    a side of the light blocker forms the sidewall surface of the microchannel, and
    a sidewall surface of the microchannel to which the antibody is fixed inclines in a direction narrowing a width of the microchannel toward the first substrate.

4. The microdevice according to claim 1, further comprising:
    a second substrate facing the first substrate; and
    a partition wall forming the microchannel by being sandwiched by the first substrate and the second substrate,
    wherein a side of the partition wall forms the sidewall surface of the microchannel.

5. The microdevice according to claim 4, wherein the light blocker is provided on the first substrate.

6. The microdevice according to claim 4, wherein the light blocker is provided at an end of the partition wall on the first substrate side.

7. A microdevice comprising:
    a microchannel to which a measurement target solution containing a measurement target substance and a fluorescence-labeled derivative acquired by fluorescence-labeling the measurement target substance is introduced;

an antibody being fixed to at least one sidewall surface of the microchannel and specifically binding to the measurement target substance and the fluorescence-labeled derivative;
a light blocker blocking excitation light exciting fluorescent light radiated by the fluorescence-labeled derivative; and
a first substrate that the excitation light enters, wherein
the measurement target substance and the fluorescence-labeled derivative specifically bind to the antibody in a competitive manner,
when the measurement target solution is introduced to the microchannel, the light blocker blocks the excitation light entering the fluorescence-labeled derivative specifically binding to the antibody, and
the light blocker is formed of a material absorbing the excitation light and the fluorescent light,
wherein a section of the microchannel in a widthwise direction has a tapered shape narrowing toward the first substrate, and
wherein the light blocker is formed of:
(i) polydimethylsiloxane containing carbon black or ferric oxide, or
(ii) polymethyl methacrylate containing carbon black or ferric oxide.

8. The microdevice according to claim 7, wherein
the antibody is a plurality of antibodies,
the measurement target solution contains a plurality of the measurement target substances and a plurality of fluorescence-labeled derivatives, and
each antibody of the plurality of antibodies specifically binds to one measurement target substance out of the plurality of the measurement target substances and one fluorescence-labeled derivative out of the plurality of fluorescence-labeled derivatives and is immobilized for each division of the sidewall surface along a lengthwise direction of the microchannel.

9. The microdevice according to claim 7,
a second substrate facing the first substrate, wherein
the light blocker forms the microchannel by being sandwiched by the first substrate and the second substrate,
a side of the light blocker forms the sidewall surface of the microchannel, and
a sidewall surface of the microchannel to which the antibody is fixed inclines in a direction narrowing a width of the microchannel toward the first substrate.

10. The microdevice according to claim 7, further comprising:
a second substrate facing the first substrate; and
a partition wall forming the microchannel by being sandwiched by the first substrate and the second substrate,
wherein a side of the partition wall forms the sidewall surface of the microchannel.

11. The microdevice according to claim 10, wherein the light blocker is provided on the first substrate.

12. The microdevice according to claim 10, wherein the light blocker is provided at an end of the partition wall on the first substrate side.

13. An analysis device comprising:
a microdevice;
an irradiator; and
a detector,
the microdevice including
a microchannel to which a measurement target solution containing a measurement target substance is introduced,
an antibody being fixed to at least one sidewall surface of the microchannel and specifically binding to the measurement target substance,
a fluorescence-labeled derivative being specifically bound to the antibody and being acquired by fluorescence-labeling the measurement target substance,
a light blocker blocking excitation light exciting fluorescent light radiated by the fluorescence-labeled derivative, and
a first substrate that the excitation light enters, wherein
the measurement target substance and the fluorescence-labeled derivative specifically bind to the antibody in a competitive manner,
the antibody is fixed to the sidewall surface of the microchannel in a state of specifically binding to the fluorescence-labeled derivative,
the light blocker blocks the excitation light entering the fluorescence-labeled derivative specifically binding to the antibody,
the irradiator irradiates the microchannel of the microdevice with the excitation light, and
the detector detects the fluorescent light,
wherein a section of the microchannel in a widthwise direction has a tapered shape narrowing toward the first substrate, and
wherein the light blocker is formed of:
(i) polydimethylsiloxane containing carbon black or ferric oxide, or
(ii) polymethyl methacrylate containing carbon black or ferric oxide.

14. The analysis device according to claim 13, wherein
the excitation light is linearly polarized light having a polarization direction in a predetermined direction, and
the fluorescent light is linearly polarized light having a polarization direction in a direction orthogonal to the predetermined direction.

15. The analysis device according to claim 13, further comprising:
a promotor promoting a competitive reaction to the antibody between the measurement target substance and the fluorescence-labeled derivative.

16. An analysis device comprising:
a microdevice;
an irradiator; and
a detector,
the microdevice including
a microchannel to which a measurement target solution containing a measurement target substance and a fluorescence-labeled derivative acquired by fluorescence-labeling the measurement target substance is introduced,
an antibody being fixed to at least one sidewall surface of the microchannel and specifically binding to the measurement target substance and the fluorescence-labeled derivative,
a light blocker blocking excitation light exciting fluorescent light radiated by the fluorescence-labeled derivative, and
a first substrate that the excitation light enters, wherein
the measurement target substance and the fluorescence-labeled derivative specifically bind to the antibody in a competitive manner,
when the measurement target solution is introduced to the microchannel, the light blocker blocks the excitation light entering the fluorescence-labeled derivative specifically binding to the antibody, the irradiator irradiates the microchannel of the microdevice with the excitation light through an opening of the light blocker, and the detector detects the fluorescent light, wherein a section of the microchannel in a widthwise direction has a tapered shape narrowing toward the first substrate, and wherein the light blocker is formed of:
(i) polydimethylsiloxane containing carbon black or ferric oxide, or
(ii) polymethyl methacrylate containing carbon black or ferric oxide.

17. The analysis device according to claim 16, wherein the excitation light is linearly polarized light having a polarization direction in a predetermined direction, and the fluorescent light is linearly polarized light having a polarization direction in a direction orthogonal to the predetermined direction.

18. The analysis device according to claim 16, further comprising:

a promotor promoting a competitive reaction to the antibody between the measurement target substance and the fluorescence-labeled derivative.

* * * * *